(12) United States Patent
Gross et al.

(10) Patent No.: US 7,377,648 B2
(45) Date of Patent: May 27, 2008

(54) VOLUMETRIC POINT SPREAD FUNCTION FOR EYE DIAGNOSIS AND TREATMENT

(75) Inventors: Erik Gross, Palo Alto, CA (US); Guangming Dai, Fremont, CA (US); Charles Campbell, Berkeley, CA (US)

(73) Assignee: AMO Manufacturing USA, LLC, Milpitas, CA (US)

( * ) Notice: Subject to any disclaimer, the term of this patent is extended or adjusted under 35 U.S.C. 154(b) by 344 days.

(21) Appl. No.: 11/064,876

(22) Filed: Feb. 22, 2005

(65) Prior Publication Data

US 2005/0213040 A1   Sep. 29, 2005

Related U.S. Application Data

(60) Provisional application No. 60/548,709, filed on Feb. 27, 2004, provisional application No. 60/546,416, filed on Feb. 20, 2004.

(51) Int. Cl.
*A61B 3/00* (2006.01)

(52) U.S. Cl. .................. 351/246; 351/205; 351/206

(58) Field of Classification Search ................ 351/246, 351/205, 206
See application file for complete search history.

(56) References Cited

U.S. PATENT DOCUMENTS

| | | |
|---|---|---|
| 5,533,997 A | 7/1996 | Ruiz |
| 5,682,223 A | 10/1997 | Menezes et al. |
| 5,684,560 A | 11/1997 | Roffman et al. |
| 5,724,258 A | 3/1998 | Roffman |

(Continued)

FOREIGN PATENT DOCUMENTS

WO   WO 95/27453 A1   10/1995

(Continued)

OTHER PUBLICATIONS

Anschutz, T. "Laser correction of hyperopia and presbyopia", Int. Ophthalmol Clin. (1994) 34(4): 107-137.

(Continued)

*Primary Examiner*—Scott J. Sugarman
*Assistant Examiner*—James R Greece
(74) *Attorney, Agent, or Firm*—Townsend & Townsend & Crew LLP; Mark D. Barrish

(57) ABSTRACT

Systems and methods analyze, diagnose, and/or treat a patient's eye using modified forms of the point spread function ("PSF") tailored to the vision system. Factors that alter perception of visual aberrations can be included and/or volumetric point spread functions calculated, often using point spread function calculations throughout a range of optical distances to more fully indicate the variation in visual perception of optics at different distances. A variety of visual affects of the human optical system can be simulated, analyzed, and modeled, including: single versus multiple wavelength sources, chromatic aberrations, retinal resolution, wavelength-dependent visual response, Stiles-Crawford effects, and/or non-linearity of retinal response. The perceived point spread function can offer objective confirmation of the patient's visual perception, allow a treating physician to see a closer approximation of what the patient sees, indicate the scale and significance of wavefront aberrations, and/or show which aberrations affect vision and which do not.

23 Claims, 50 Drawing Sheets
(46 of 50 Drawing Sheet(s) Filed in Color)

U.S. PATENT DOCUMENTS

| | | | |
|---|---|---|---|
| 5,835,192 | A | 11/1998 | Roffman et al. |
| 5,864,379 | A | 1/1999 | Dunn |
| 5,928,129 | A | 7/1999 | Ruiz |
| 6,059,775 | A | 5/2000 | Nielsen |
| 6,280,435 | B1 | 8/2001 | Odrich et al. |
| 6,361,170 | B1 | 3/2002 | Bille |
| 6,452,145 | B1 | 9/2002 | Graves et al. |
| 6,554,429 | B1 | 4/2003 | Campin et al. |
| 6,607,274 | B2 | 8/2003 | Stantz et al. |
| 6,679,606 | B2 | 1/2004 | Campin et al. |
| 2003/0095256 | A1* | 5/2003 | Cargill et al. ............... 356/328 |
| 2005/0024585 | A1* | 2/2005 | Dai ............................ 351/205 |

FOREIGN PATENT DOCUMENTS

| | | |
|---|---|---|
| WO | WO 02/07660 | 1/2002 |
| WO | WO 02/34178 | 5/2002 |
| WO | WO 02/085231 | 10/2002 |
| WO | WO 2004/053568 A1 | 6/2004 |

OTHER PUBLICATIONS

Artal, Pablo. Calculation of two-dimensional foveal retinal images in real eyes. J. Opt. Soc. Am. A, vol. 7, No. 8 (Aug. 1990), pp. 1374-1381.

Greivenkamp, John E. et al. Visual Acuity Modeling Using Optical Raytracing of Schematic Eyes. American Journal of Ophthalmology, vol. 120, No. 2 (Aug. 1995), pp. 227-240.

Liang, Junzhong et al, Aberrations and retinal image quality of the normal human eye. J. Opt. Soc. Am. A. vol. 14, No. 11 (Nov. 1997), pp. 2873-2883.

International Search Report.

* cited by examiner

Fig. 1A
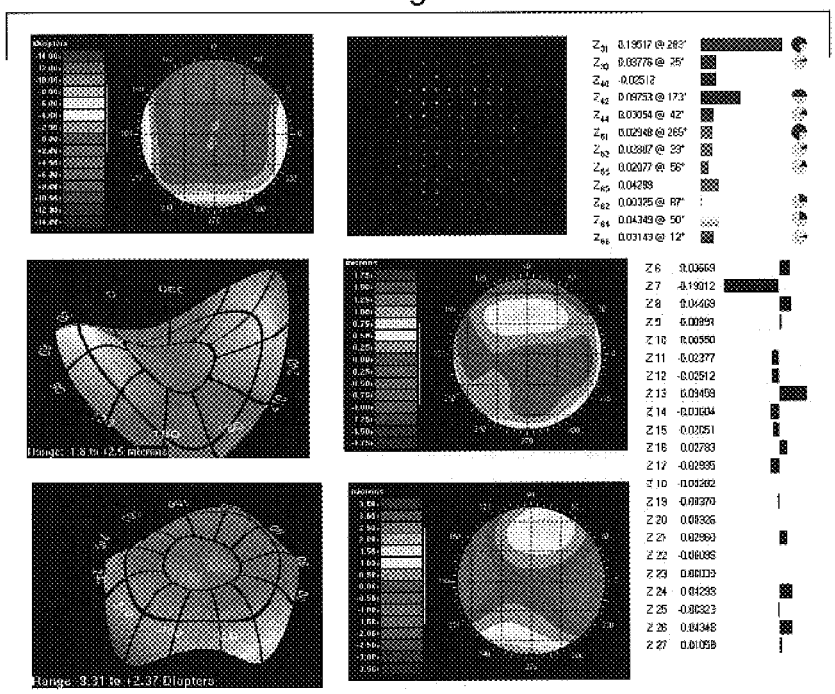
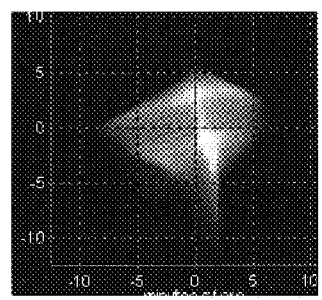
Fig. 1B

Fig. 2A
Myopic
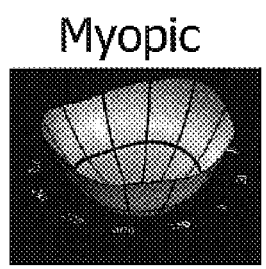
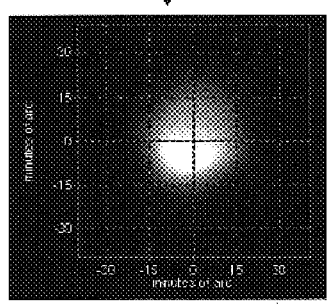
Fig. 2B
Astigmatic
(Pure Cylinder)
Fig. 2C
Emmetropic
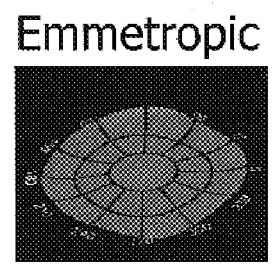
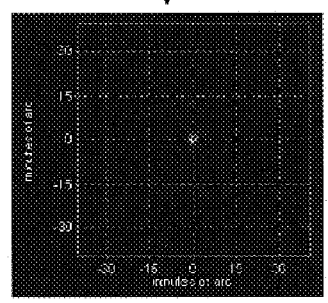

Fig. 5
Eye with Myopia
| | Diffractive PSF | Geometric PSF |
|---|---|---|
| All Aberrations | 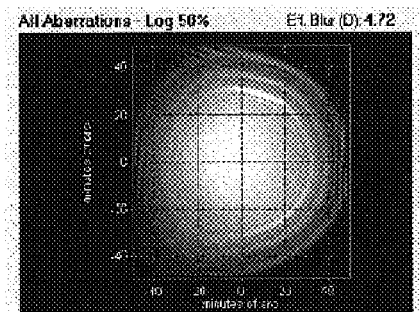 | 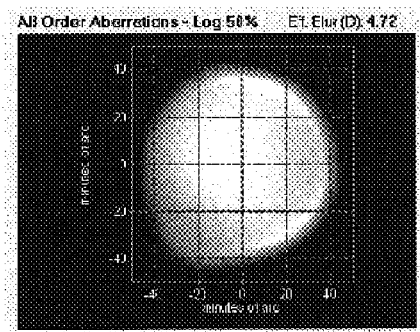 |
| High Order Aberrations | 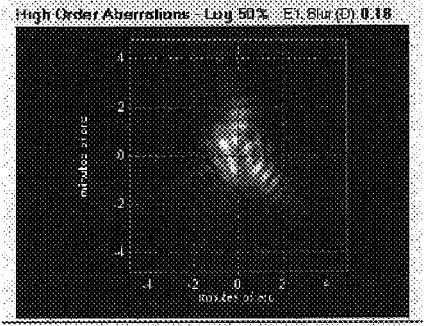 | 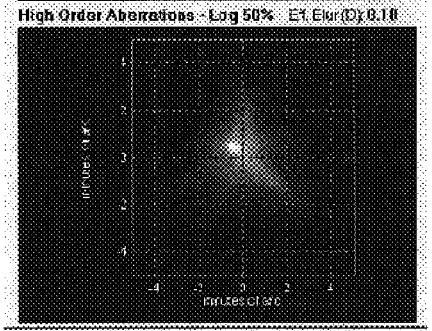 |

Eye with Myopia

High Order Aberrations

Stiles-Crawford Effect
Without Stiles-Crawford
With Stiles-Crawford
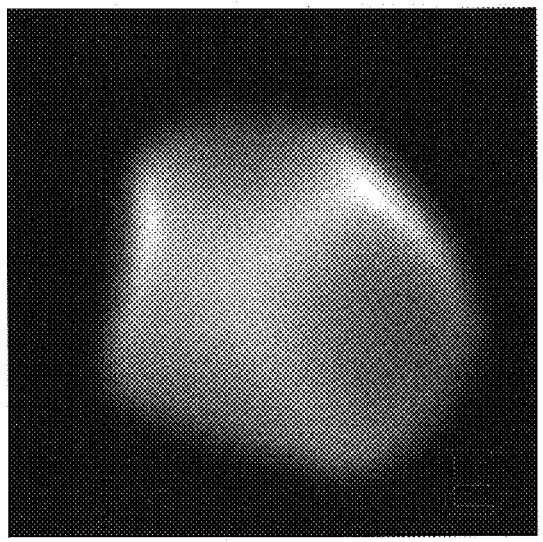
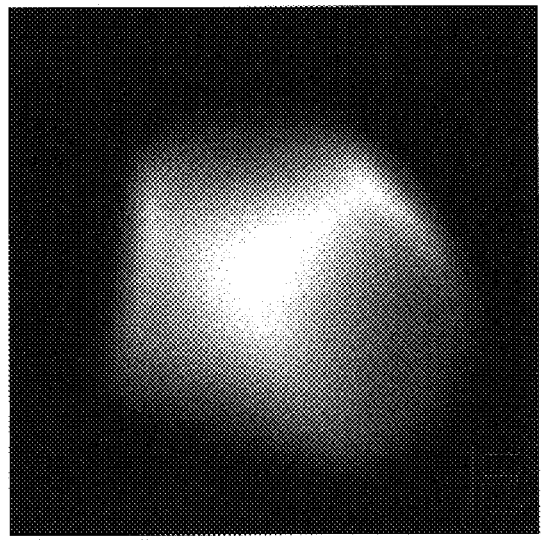
Fig. 10C
Fig. 10D Linear Logarithmic Logarithmic with
Saturation Fig. 22A    Fig. 22B    Fig. 22C    Fig. 22D
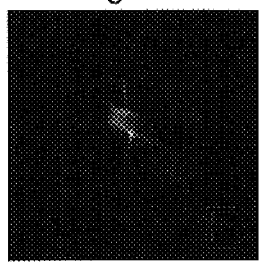 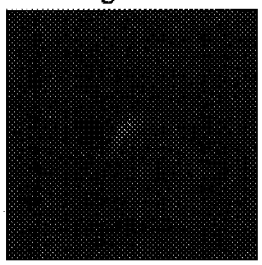 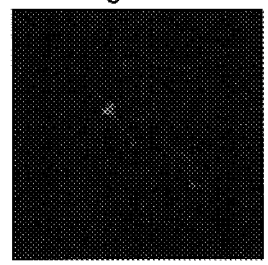 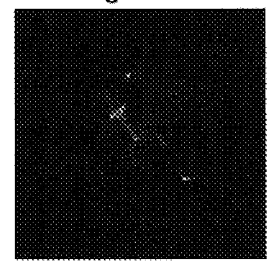
White Light (Solar Spectrum)    Blue LED 480 nm (Broad)    Red LED 665 nm (narrow)    Sodium 590 nm
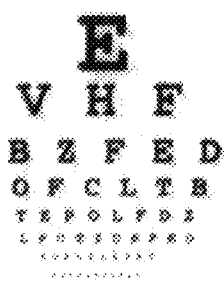 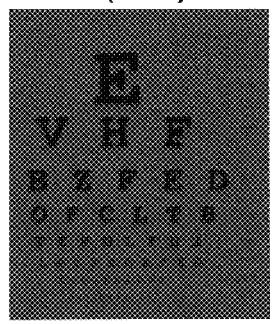 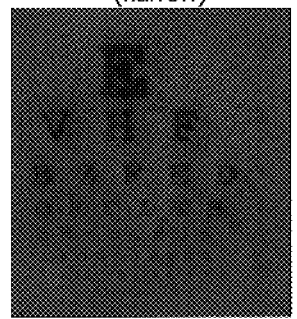 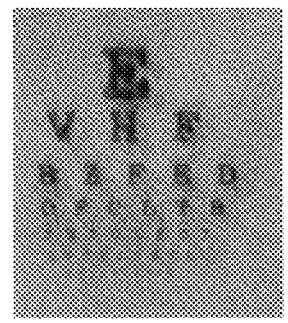
Fig. 22E    Fig. 22F    Fig. 22G    Fig. 22H Fig. 24A
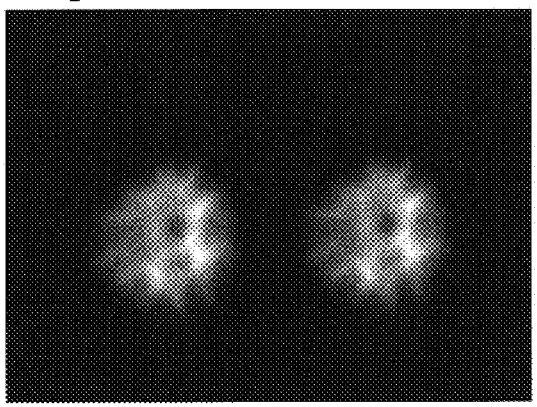
Halogen
color temp=3000K
Fig. 24B
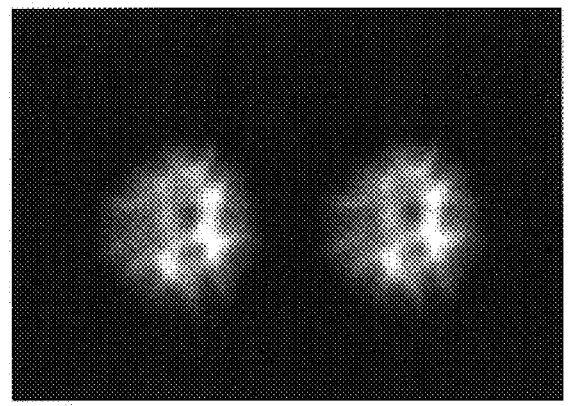
Xenon HID
color temp=5200K
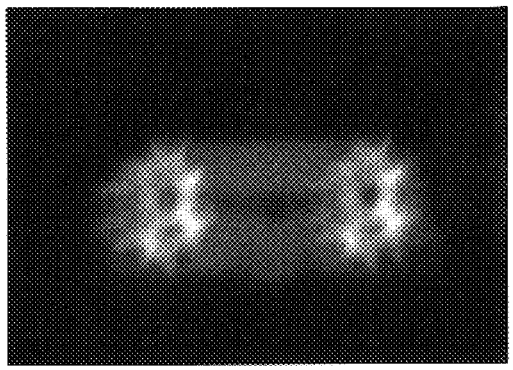
Fig. 25A
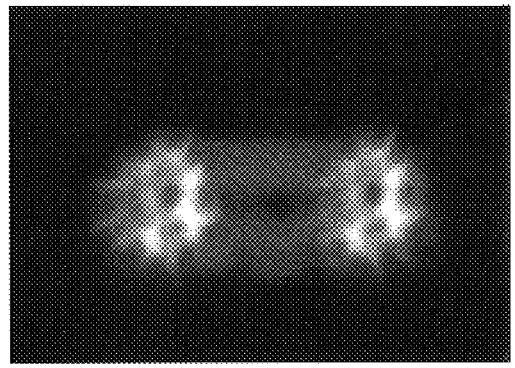
Fig. 25B Fig. 27A
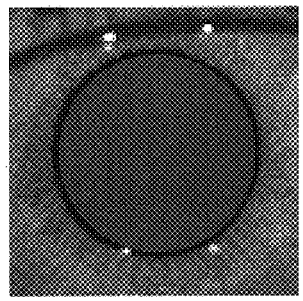
Fig. 27C
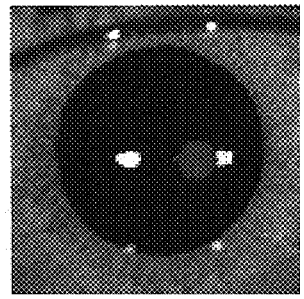
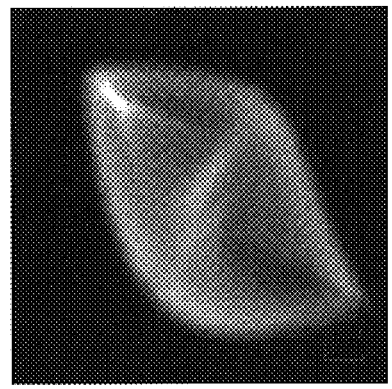
Fig. 27B  Full PSF
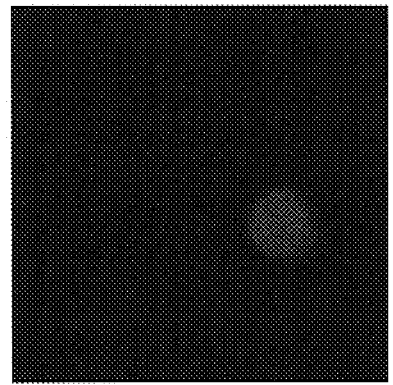
Partial PSF  Fig. 27D Fig. 27E
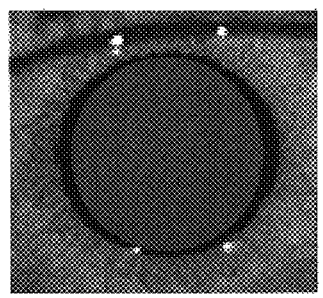
Fig. 27G
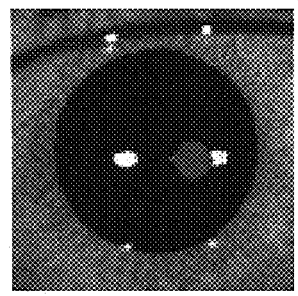
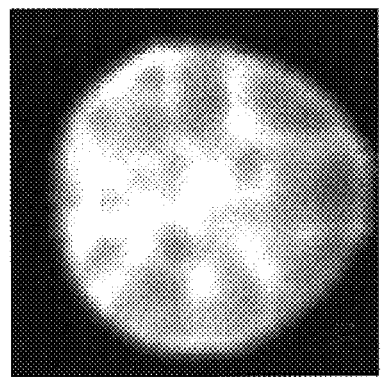
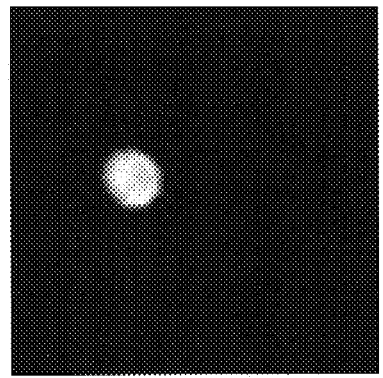
Fig. 27F  Full PSF
Partial PSF  Fig. 27H Fig. 27I
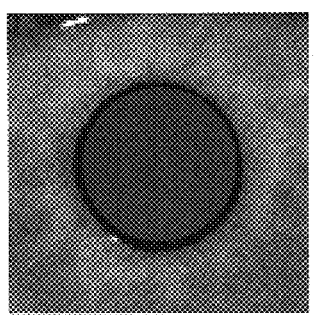
Fig. 27K
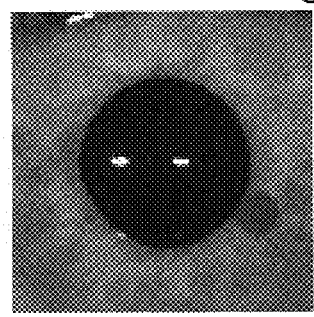
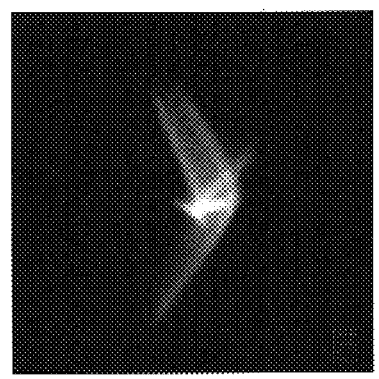
Full PSF
Fig. 27J
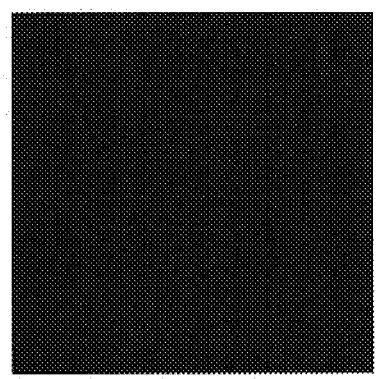
Partial PSF
Fig. 27L VPSF: Presbyopic Treatment PreOp PostOp Fig. 35A
Distance Pre
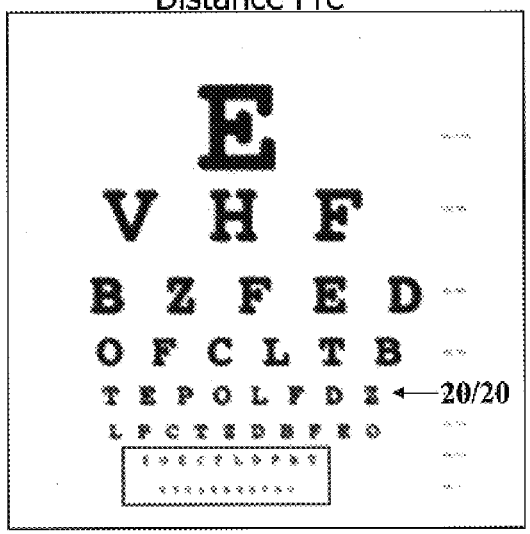
Fig. 35C
Distance Post
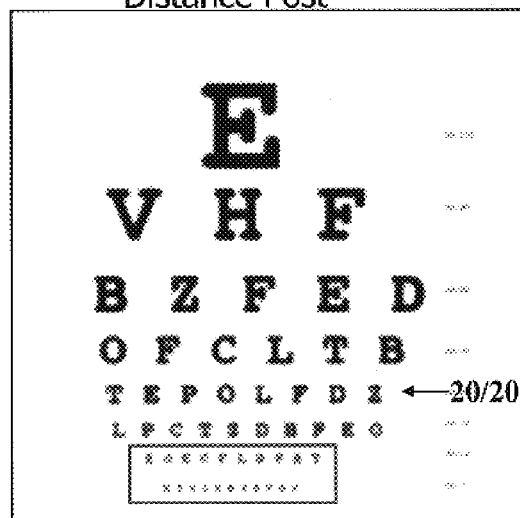
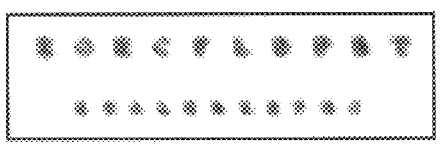
Fig. 35B
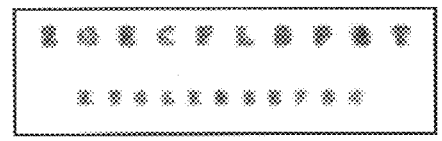
Fig. 35D Fig. 35E
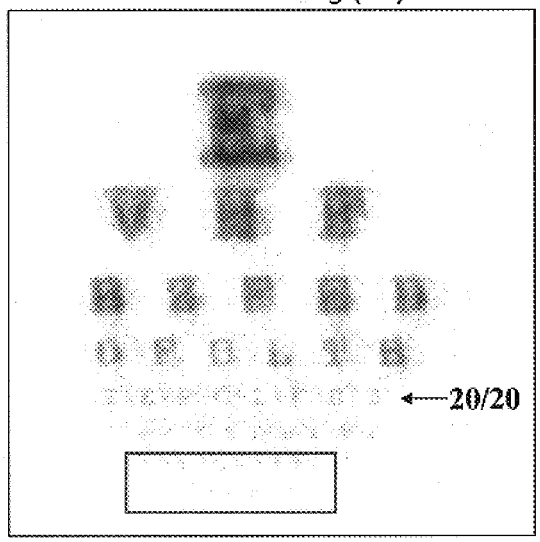
Fig. 35G
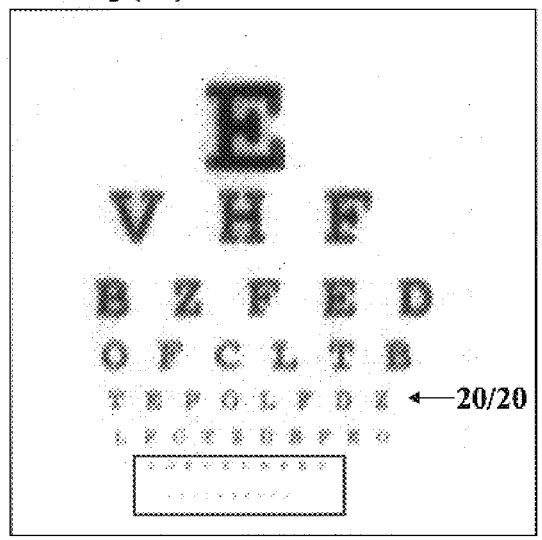
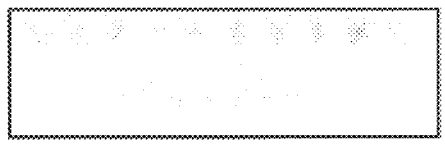
Fig. 35F
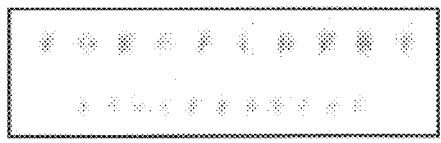
Fig. 35H Schematic diagram of eye model with an aspheric correcting lens for on-axis retinal imaging.

TABLE 4.
Correcting lens parameters for on-axis correction.

| Surface No. | Radius (mm) | Conic Constant | Thickness (mm) | Refractive Index |
|---|---|---|---|---|
| 1 | 6.502 | −0.085 | 3.957 | 1.606 |
| 2 | 5.006 | 0.053 | 5.0 | 1.0 |

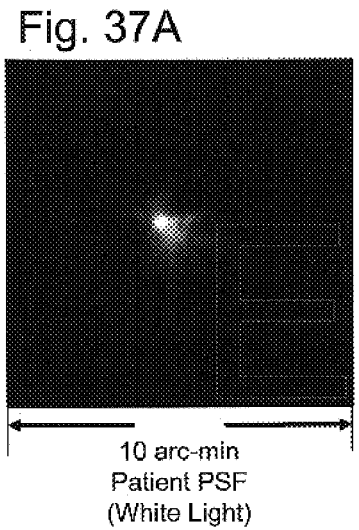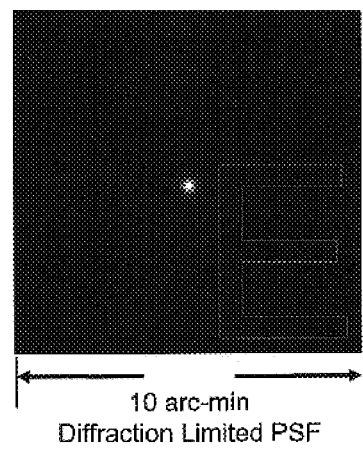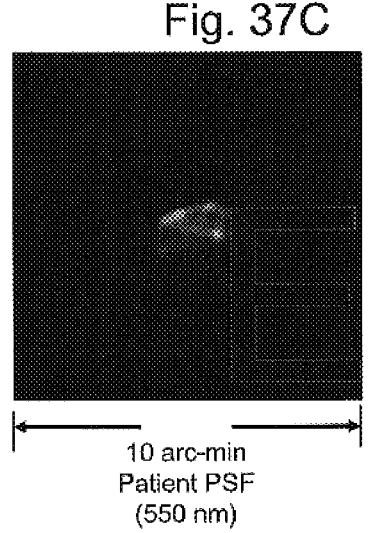
Fig. 37A — 10 arc-min Patient PSF (White Light)
Fig. 37B — 10 arc-min Diffraction Limited PSF
Fig. 37C — 10 arc-min Patient PSF (550 nm)

Scale Issues
Fig. 39A
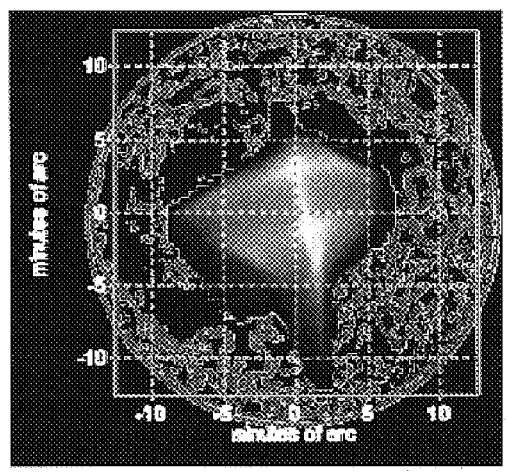
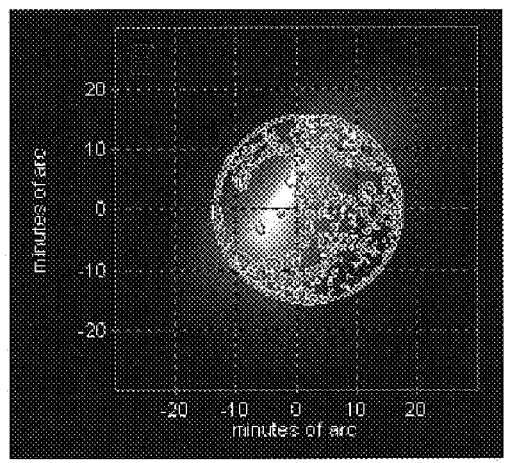
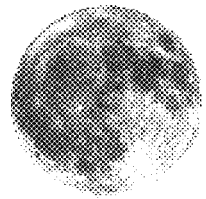

PSF Zoom
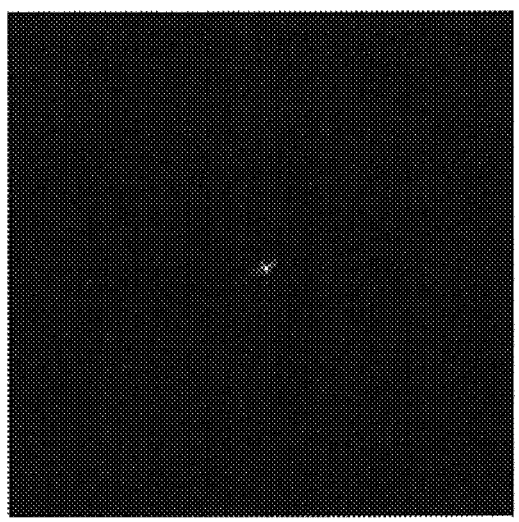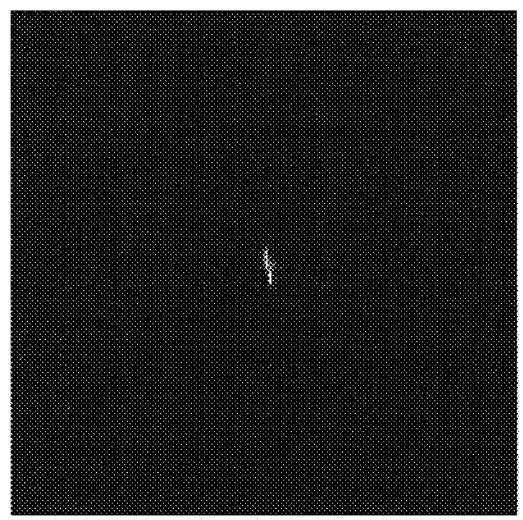
Fig. 40

VOLUMETRIC POINT SPREAD FUNCTION FOR EYE DIAGNOSIS AND TREATMENT

CROSS-REFERENCES TO RELATED APPLICATIONS

This application claims the benefit of priority from U.S. Provisional Patent Application No. 60/546,416, filed Feb. 20, 2004; and from U.S. Provisional Patent Application No. 60/548,709, filed Feb. 27, 2004; both entitled "Volumetric Point Spread Function for Eye Diagnosis and Treatment," the full disclosures of which are incorporated herein by reference.

STATEMENT AS TO RIGHTS TO INVENTIONS MADE UNDER FEDERALLY SPONSORED RESEARCH AND DEVELOPMENT

Not Applicable

REFERENCE TO A "SEQUENCE LISTING," A TABLE, OR A COMPUTER PROGRAM LISTING APPENDIX SUBMITTED ON A COMPACT DISK

Not Applicable

BACKGROUND OF THE INVENTION

This invention generally relates to optical system analysis, and in particular embodiments provides methods and systems for evaluating and/or treating an eye of a patient, generally through the use of point spread functions tailored to model the patient's visual perception. Other embodiments make use of volumetric point spread functions spread throughout an imaging distance range. Graphical representations of perceived point spread function and/or volumetric point spread functions can validate a patient's perception, and may be used to develop a specific prescription for the patient or new classes of refractive corrections for a number of patients.

An individual's visual perception can be measured in a variety of different ways, and can be affected by a number of different factors. Visual acuity is among the more common visual perception measurements. Traditionally, measuring visual acuity of the human eye has involved using eye charts. Visual acuity measurements can be affected by objective factors such as the optical characteristics of the cornea and lens, as well as subjective factors such as light absorption and detection in the retina, neural processing in the brain, and the like. While visual acuity measurements can provide a good overall measurement of visual perception capabilities, they provide little guidance regarding the specific defects or weaknesses of the visual system which might be limiting visual perception for a particular patient.

More recently, objective measurements of optical performance of the eye have been made possible. Wavefront measurements using Hartmann-Shack sensors now allow optical aberrations to be measured across the optical system. From these aberration measurements, a variety of objective optical performance characteristics may be calculated. These objective optical aberration measurement and calculated performance characteristics have significantly advanced the art of diagnosing and treating a patient's optical tissues over the last several years. It is now common, for example, for aberration measurements of a patient to be used for developing custom prescriptive refractive corrections for the patient's eye, with these prescriptions often being imposed using laser eye surgery. By combining the new objective aberration measurement techniques with the laser refractive correction capabilities of laser eye surgery, many patients can have both lower order optical errors (such as myopia, hyperopia, and astigmatism) and higher order aberrations partially and/or substantially fully corrected, thereby providing many patient's with visual acuities of greater than 20/20.

As with many such successes, however, still further improvements would be desirable. In particular, the known objective visual performance characteristics now being calculated from aberration data do not capture many of the subtleties of the human vision system. Wavefront measurements and calculated aberration characteristic displays, for example, are often not intuitively understood by the great majority of patients.

In light of the above, it would be generally desirable to provide enhanced systems and methods for diagnosing, analyzing, and treating aberrations of a patient's eye. It would also be beneficial to provide enhanced visual perception effect models and graphical representations which more precisely match the patient's perception. It would be particularly advantageous if these improvements could make use of the objective aberration measurements now available and could both more closely model the patient's perception from their visual system.

BRIEF SUMMARY OF THE INVENTION

The present invention generally provides improved systems and methods for analyzing, diagnosing, and/or treating a patient's eye. In many embodiments, the invention makes use of one or more modified forms of the point spread function ("PSF"). These modified point spread functions will often be tailored to the vision system, rather than relying entirely on standard methods for calculating a point spread function, which may be based on long-standing optical techniques suited to astronomy and laser science, but which may not necessarily capture the subtleties of the human visual system. Factors that alter perception of visual aberrations can be included in the modified point spread function calculations. In some embodiments, volumetric point spread functions are calculated, often using point spread function calculations within a range of optical distances so as to more fully indicate the variation in visual perception as objects at different distances are viewed and/or as the eye accommodates to viewing at different distances. A variety of visual effects of the human optical system can be simulated, analyzed, modeled, and displayed, including: single versus multiple wavelength sources, chromatic aberrations, retinal resolution, wavelength-dependent visual response, Stiles-Crawford effects, and/or non-linearity of retinal response. By appropriately modeling one, some, or all of these effects, a perceived point spread function can be calculated that offers objective confirmation of the patient's visual perception, allows a treating physician to see a closer approximation of what the patient sees, indicates the scale and significance of wavefront aberrations, shows which aberrations affect vision and which do not, and/or provides a validating experience for the patient who has lived with visual ghosting, halos, or flares by allowing the patient to see an objective graphical representation of their visual perception as caused by their specific aberrations.

In a first aspect, the invention provides a system for evaluating or treating an eye. The system comprises an input for receiving an optical aberration signal. A module is coupled to the input and determines the volumetric point spread function from the aberration signal. An output is coupled to the module, and the output transmits signals in response to the volumetric point spread function.

In many embodiments, the input will be coupled to a wavefront sensor. The output signals may indicate an optical performance of the eye. The output may be coupled, for example, to a refractive laser system or other eye treatment apparatus. In such embodiments, the module may comprise at least a portion of the processor, with the processor deriving a pattern of laser energy to improve refractive performance of the eye in response to the output signals from the module.

The volumetric point spread function will typically comprise a point spread function at a plurality of locations spread throughout a distance range from a cornea of the eye. The retina is often disposed within or near the distance range. The point spread function locations may be at discreet distances within the range, or may be spread continuously throughout some or all of the range.

In some embodiments, the module may determine the volumetric point spread function at a plurality of different pupil sizes. This may be useful, for example, when analyzing the visual perception associated with a range of different viewing distances, as the pupils will often contract and/or expand with changes in viewing distance. The module may determine the volumetric point spread function at photopic and/or scotopic conditions. Alternative ambient lighting conditions between these two may also be employed. In many embodiments, the output signals will correspond to a graphical representation of the volumetric point spread function. The graphical representation may correspond to perceived vision of the patient. So as to enhance correlation between the perceived vision and the volumetric point spread function, the module may be configured to generate the volumetric point spread function by modeling polychromatic source light, chromatic aberration of the eye, wavelength-dependent visual response, adjustable pupil size, Stiles-Crawford effect, and/or non-linear retinal response. In many embodiments, the module may be configured to generate a post-treatment volumetric point spread function, with the graphical representation allowing a comparison between the volumetric point spread function and the post-treatment volumetric point spread function. This comparison may help when selecting between a plurality of alternative treatments, or may be used to derive a preferred treatment prescription. The post-treatment volumetric point spread function will preferably indicate an extension of reading range by at least about 2 diopters.

In another aspect, the invention provides a system for evaluating or treating an eye of a particular patient. The eye has optical aberrations, and the system comprises an input for receiving an optical aberration signal corresponding to the aberration of the eye. A module is coupled to the input, and is configured to determine a perceived point spread function from the aberration signal by modeling chromatic aberration of the eye and adjustable pupil size. An output coupled to the module transmits signals in response to the perceived point spread function.

The module may also be configured to model polychromatic source light, wavelength-dependent visual response (such as to photopic and scotopic conditions) and/or non-linear retinal response. The module may optionally be configured to model each of these three effects. In some embodiments, the module may model Stiles-Crawford effect, although some embodiments do not do so.

Optionally, the system may also include a graphical display coupled to the output. The graphical display may illustrate the perceived point spread function so as to model visual perception of the patient in response to an image, often in response to a point light source. The graphical display may optionally present images illustrating visual perception of other source images, including Snellen eye charts, other visual test images, real-world images, or the like. In some embodiments, a graphical display may illustrate the perceived point spread function at a plurality of locations throughout a distance range, with the retina of the patient being disposed in or near the distance range relative to a cornea of the patient so that the perceived point spread function comprises a volumetric point spread function.

In another aspect, the invention provides a method for evaluating or treating an eye of a particular patient. The eye has optical aberration, and the method comprises identifying the optical aberration of the eye. A perceived point spread function or a volumetric point spread function is determined from the aberration, and is graphically displayed.

Optionally, the graphical display may be shown to the patient to objectively validate the patient's perception and/or the point spread function determined in the method. In some embodiments, a refractive treatment prescription may be developed using the graphical display, either solely for that specific patient or for a plurality or class of patients.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1A illustrates 8 alternative views or forms of presenting aberrations, with the same aberrations being represented in each view.

FIG. 1B illustrates a point spread function of the aberration illustrated in FIG. 1A.

FIGS. 2A-2C illustrate different eye types and associated point spread functions.

FIG. 5 illustrates a comparison of point spread functions determined using diffractive versus geometric approaches.

FIGS. 10A-10D illustrate effects of Stiles Crawford effect on point spread functions.

FIGS. 21-26 illustrate color image convolutions and methods therefore using point spread functions and different light spectra.

FIGS. 27A-27M illustrate partial point spread functions and analysis of point spread functions of a selected portion of the pupil.

FIGS. 35A-35H illustrate Snellen eye charts convolved using point spread functions used in the volumetric point spread functions of 34A-34C so as to indicate near and far visual acuity of the patient before and after the presbyopia treatment.

FIGS. 37A-37C illustrate point spread functions having different Strehl ratios to help determine how meaningful the Strehl ratio may be.

FIGS. 39A and 39B illustrate point spread functions and associated scale issues.

FIG. 40 illustrates point spread function zoom.

DETAILED DESCRIPTION OF THE INVENTION

Figure 2:
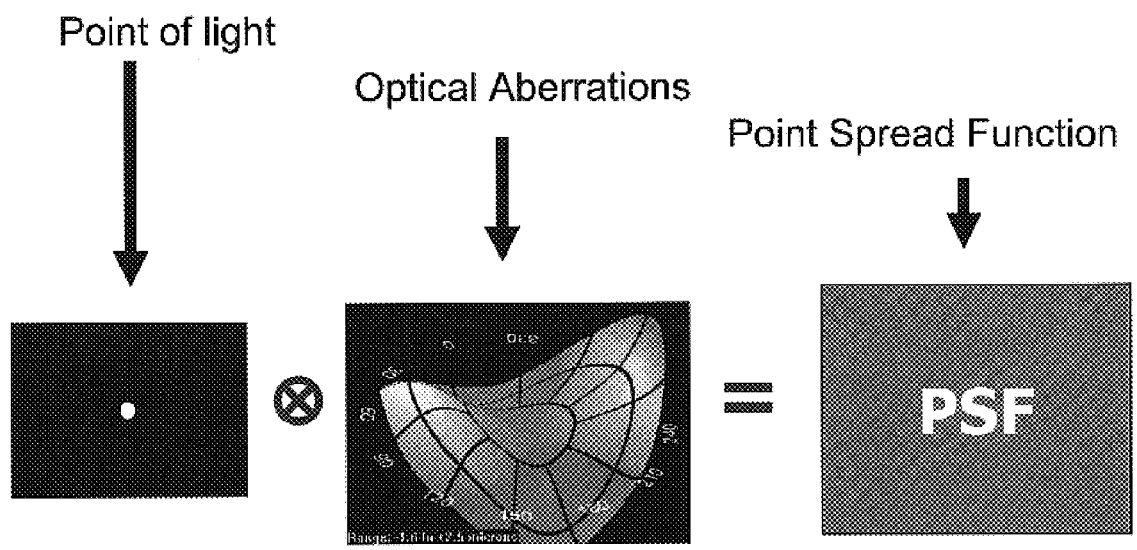
FIG. 2 schematically illustrates how to determine a point spread function and what information is conveyed thereby.

The present generally provides improved systems and methods for analysis and/or treatment of a patient's vision. In many embodiments, the invention makes use of aberration data for a particular patient, with the aberration data often being provided using a wavefront sensor. The invention often makes use of a point spread function ("PSF"), and in general provides improvements in the calculation and visualization of aberration data (and particularly wavefront-data driven point spread functions).

While a wide variety of parameters may be determined to help characterize aberration information, the point spread function has particular advantages. For example, the point spread function can help allow physicians to see aberrations as the patient sees them. Known methods for calculating a point spread function are often based on long-standing optical techniques. These methods may have been derived from and/or are suited to use in astronomy and laser science, but do not always capture the subtleties of the human vision system. By analyzing factors that alter perception of visual aberrations and establishing methods for incorporating these factors in a perceived and/or volumetric point spread function calculation, improvements in the calculation and visualization of performance of the vision system may be provided.

The following perceived volumetric point spread function effects are simulated in the figures attached hereto and analyzed herein below: Single wavelengths versus multiple wavelengths; chromatic aberration; retinal resolution; wavelength-dependent visual response; Stiles-Crawford effect; and non-linearity of retinal response. The impact of each of these effects on individual visual perception is characterized herein based on ocular physiology and the underlying associated physical principles. Techniques can improve the point spread function so as to represent any one, a combination of any two or more, and/or all of these effects more accurately.

As indicated by the drawings and associated descriptions herein, the point spread functions were notably and significantly altered by each of the above-listed effects. The changes in the point spread functions were most noticeable for patients with significant higher-order aberrations. The most dramatic changes in the point spread function occurred when chromatic aberration and multiple wavelength effects were added to the mathematical models.

In many embodiments, the systems and methods described herein build a better point spread function, providing improvements in the calculation and visualization of wavefront-driven point spread functions. Referring now to FIG. 1A, there are many ways to visualize aberrations of the human eye. FIG. 1A illustrates eight different views of the same aberrations. Unfortunately, wavefront aberrations are not intuitively understood by some, most, or all patients. Wavefront aberration data allows calculations of highly accurate aberration elevation maps, Zernike polynomial coefficients representing the aberrations, and a wide variety of alternative aberration data and graphical representation formats. Terms such as Zernike pentafoil, secondary coma, or peripherally retarded wavefront are often meaningless to the great majority of patients.

Referring now to FIGS. 1B and 1A, the wavefront-generated point spread function illustrated in FIG. 1B is a more concrete concept that can more easily be understood by many patients. The role of the point spread function is to quickly capture the scale and significance of wavefront aberrations. Point spread functions show the aberrations that affect vision and hides those aberrations which do not. The point spread function thereby helps distill aberrations down to their essence, and conveys the interaction between different aberrations.

Seeing the point spread function can be a validating experience for the patient who has lived with visual ghosting, halos, or flares. Such patients can describe systems verbally, but can have difficulty in truly conveying what they see. The point spread function offers objective confirmation by allowing the doctor to more nearly see what the patient sees. This ability to recreate what a patient will see may allow the point spread function to be used to, at least in part, approximate visual acuity measurements as more fully described in application Ser. No. 10/871,344, filed on Jun. 18, 2004, and entitled: "Systems and Methods for Prediction of Objective Visual Acuity Based on Wavefront Measurements." Along with such overall measurements, the point spread function may also allow identification and analysis of visual symptoms from optical defects of the patient's eye. Not only does it allow the point spread function to offer validation to the patient, these capabilities may also allow confirmation that the aberration measurements are accurate and provide an appropriate basis for deriving a prescriptive treatment.

Referring now to FIG. 2, point spread functions generally reflect the results of imaging a point of light through the optical aberrations of an optical system. As illustrated in FIGS. 2A, 2B, and 2C, point spread functions can graphically illustrate the results of imaging a point source through a myopic eye, an astigmatic eye, and an emmetropic eye, respectively. Although standard methods for generating a point spread function may be used in some embodiments described herein, they are often inadequate because they do not reflect the true visual experience of some or all patients. Hence, it would often be desirable to more nearly calculate the image that a person would realistically perceive if they looked at a point source of light. Toward that end, an ideal perceived point spread function may be functionally defined as an image a person will perceive when looking at a point source of light. This ideal functional definition may not be fulfilled by all perceived point spread functions described herein, and many of the perceived point spread functions described herein will include only partial improvements over a standard point spread function. Nonetheless, the perceived point spread functions of the present invention will generally provide improvements over standard point spread functions in modeling visual perception, with the term "perceived point spread function" encompassing point spread functions that are based on a standard calculation but have been modified so as to more accurately model visual perception.

Improvements to standard point spread functions that allow the visual perception to more nearly be objectively created include modeling of multiple wavelengths, chromatic aberration, non-linear sensitivity, clone response to wavelengths, diffraction limits, and retinal resolution. Before adjusting these modifications, it is worth briefly noting that the standard point spread function may be calculated, for example, using the Fraunhofer approximation;

$$PSF(ix, iy) = K \cdot \left| FT\left(P(x, y)e^{-i\frac{2\pi}{\lambda} \cdot WaveFront(x,y)}\right) \right|^2 \quad (1)$$

Figure 3:
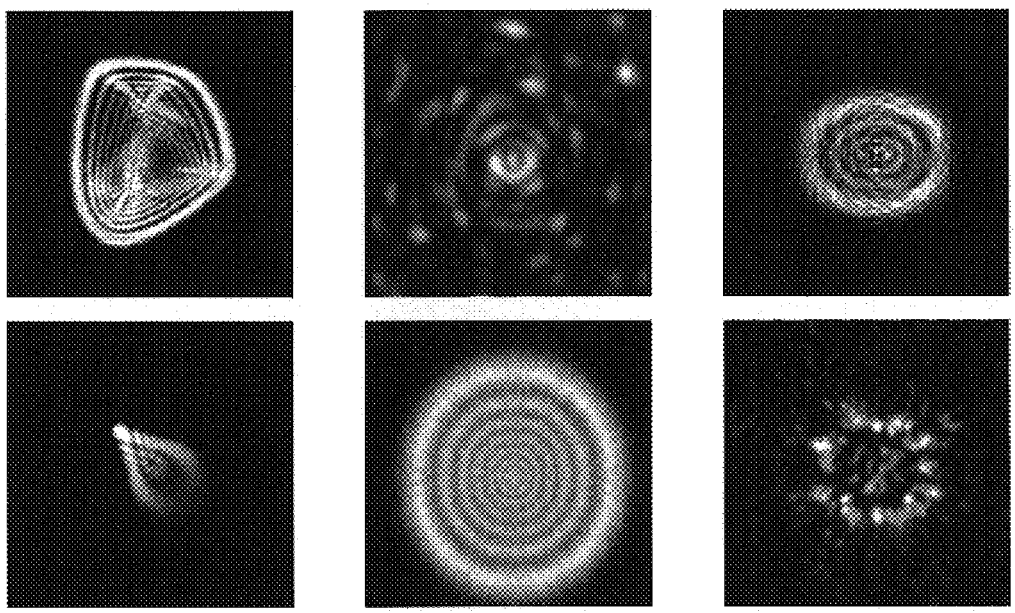
FIG. 3 graphically illustrates standard point spread functions calculated using the Fraunhofer approximation.

This calculated approximation of the point spread function can be quite useful, but as can be seen in the various point spread functions illustrated in FIG. 3, such approximations often include large numbers of fringes and the like which may differ to some extent from actual visual perception. The Fraunhofer approximation provides a standard point spread function which approximates the point spread function of monochromatic coherent light. This approximation is easy to calculate, but the eye does not satisfy the approximation conditions in at least some cases. The Fraunhofer approximation is valid only for small aberrations, and does not scale easily. Moreover, as can be understood with reference to FIG. 3, the resulting point spread functions do not always look realistic.

Figure 4:
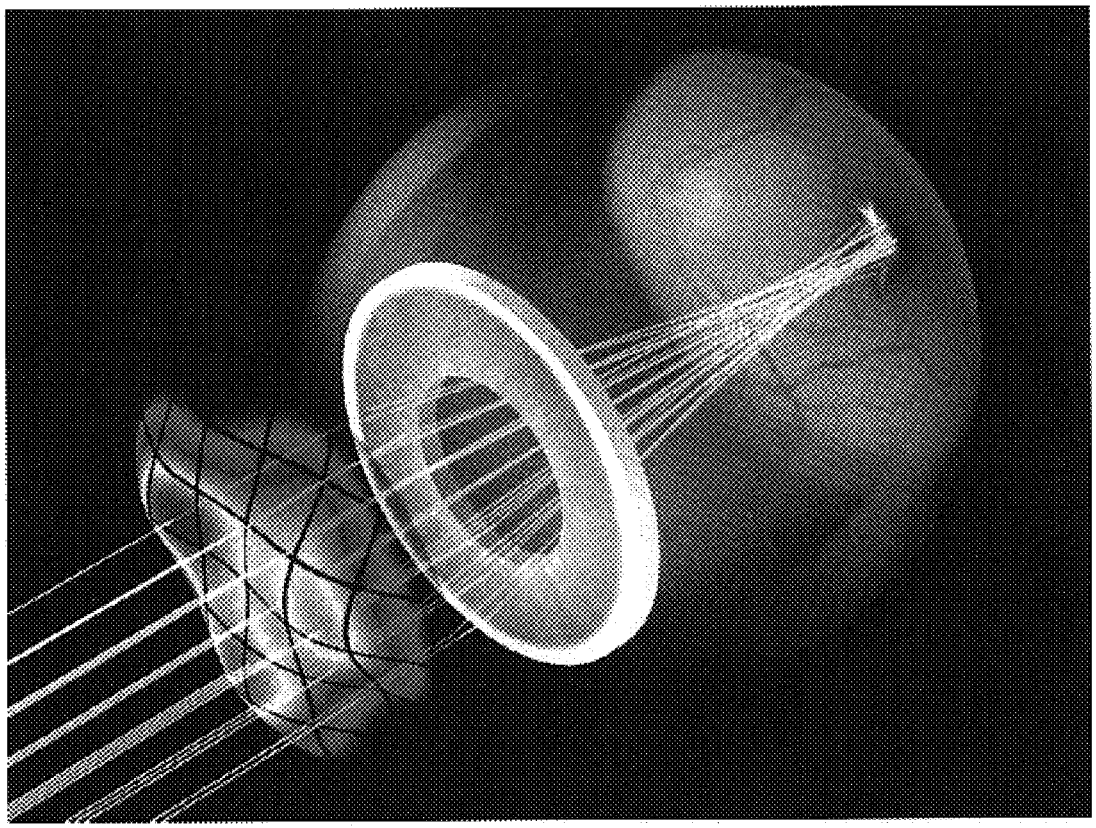
FIG. 4 illustrates a simplified model of the eye and method for calculation of optical properties thereof using a geometric approach.

Alternative methods for calculating the point spread function include the geometric ray tracing methodology schematically illustrated in FIG. 4. Such point spread functions can be calculated and/or defined in different ways. For example, a point spread function may be defined as the probability density that a photon will hit the imaging device at a point that is displaced by a vector from where it would have hit it in the absence of aberrations. Such a point spread function my be calculated as follows:

$$\epsilon_{obs}(r) = \int P(r-r')\epsilon_i(r')d^2r' = [P\hat{x}_i(r)]$$

Still further alternative definitions include the intensity distribution of a point source as imaged through the optical system; or the observed non-pointlike shape of a real point source. As can be understood with reference to the comparison between diffractive point spread functions and geometric point spread functions provided in FIG. 5, such geometric approaches can yield different but related results. Nonetheless, these geometric approaches also have limitations, sometimes including the computational difficulties and/or modeling limitations of internal optical components of the eye. A simplified mathematical model of the eye which may be used for some of these PSF calculations is schematically illustrated in FIG. 3.

Figure 6A:
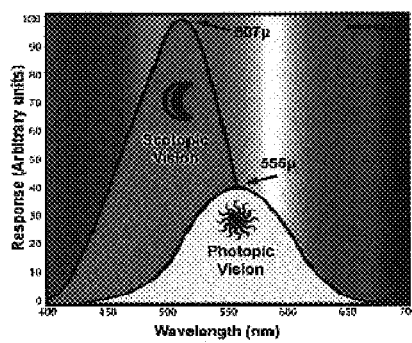
FIG. 6A illustrates retinal response to different wavelengths of light, showing that not all wavelengths result in the same response and that wavelength response may shift as conditions change between scotopic and photopic conditions, as can be used in determining visual perception effects including chromatic aberration.
Figure 6B:
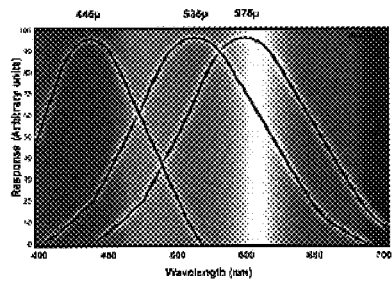
FIG. 6B illustrates cone response to different wavelengths of light.

Referring now to FIGS. 6A and 6B, chromatic aberrations may have significant effects on the perceived vision as altered by optical aberrations of the eye. As can be understood with reference to FIG. 6A, not all wavelengths are equal, as the eye's response to light varies with the wavelength of that light. In fact, the wavelength-response of the vision system varies with ambient lighting conditions, providing a peak response for wavelengths of about 155 microns with bright light photopic vision, and a narrower response peak at 507 nm under low light scotopic vision conditions.

In addition to the differences in wavelength response under different viewing conditions, the various cone responses to wavelengths may also alter the visual perception. Individual peaks of the cones are located at 445 nm, 535 nm, and 575 nm. The cone response at and away from these peaks can be readily incorporated into the calculated point spread functions.

Figure 7A:
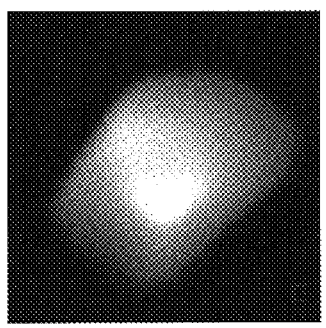
FIGS. 7A and 7B illustrate polychromatic point spread functions calculated by modeling chromatic aberration using 17 wavelengths of light in the range from 450 to 640 nm.
Figure 7B:
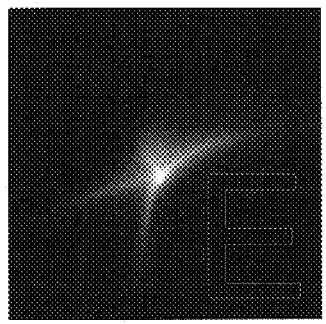

To show the effects of color point spread functions, first consider the single wavelength point spread functions illustrated in FIG. 7A (for an eye with myopia) and in FIG. 7B (for an eye having high-order aberrations). In these and other point spread functions illustrated herein, an "E" superimposed adjacent the point spread function illustrates a Snellen 20/20 eye chart letter, thereby giving an indication of the scale of the point spread function. In the myopic point spread function of FIG. 7, the entire width of the illustration is 80 arc-min, while in the high order aberration point spread function of FIG. 7B, the illustration has a width of 12 arc-min.

Figure 8A:
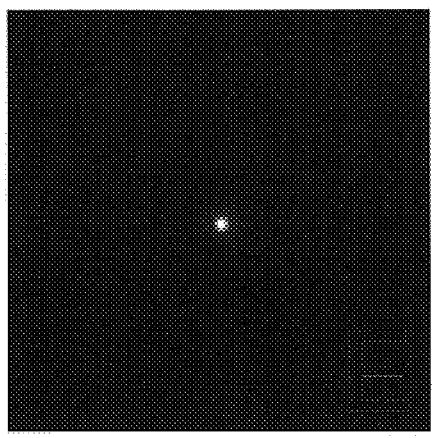
FIGS. 8A-8D illustrate color point spread functions.
Figure 8B:
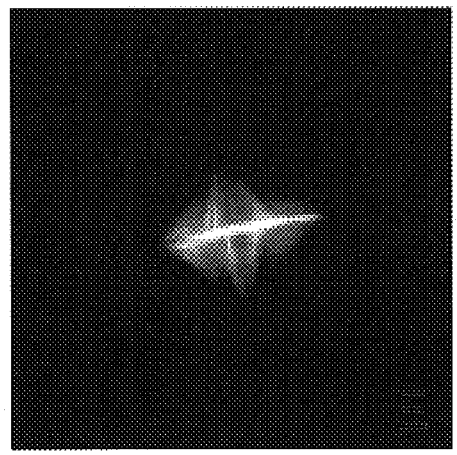
Figure 8C:
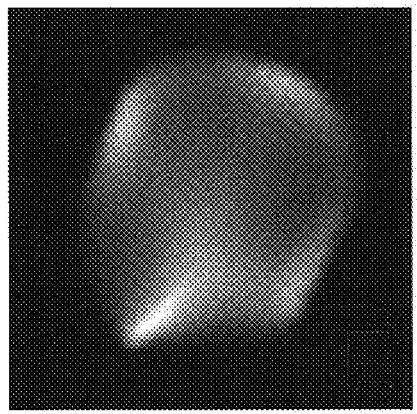
Figure 8D:
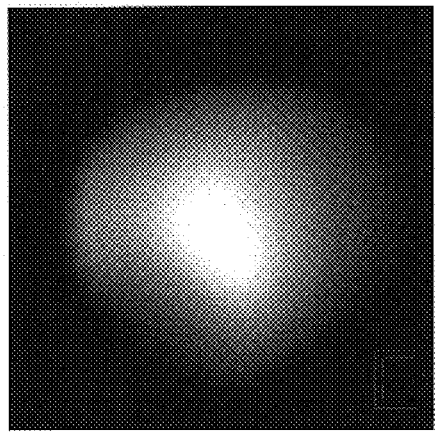

For comparison to the single color point spread functions of FIGS. 7A and 7B, FIGS. 8A through 8D illustrate point spread functions in which multiple wavelength effects are modeled. In FIG. 8A, a diffraction limited point spread function shows limited multiple wavelength effects. However, a point spread function for mixed stigmatism as illustrated in FIG. 8B shows significant multiple wavelength effects. Multiple wavelength point spread functions for a hyperopic eye are illustrated in FIG. 8C, and for a myopic eye are illustrated in FIG. 8D.

Figure 9A:
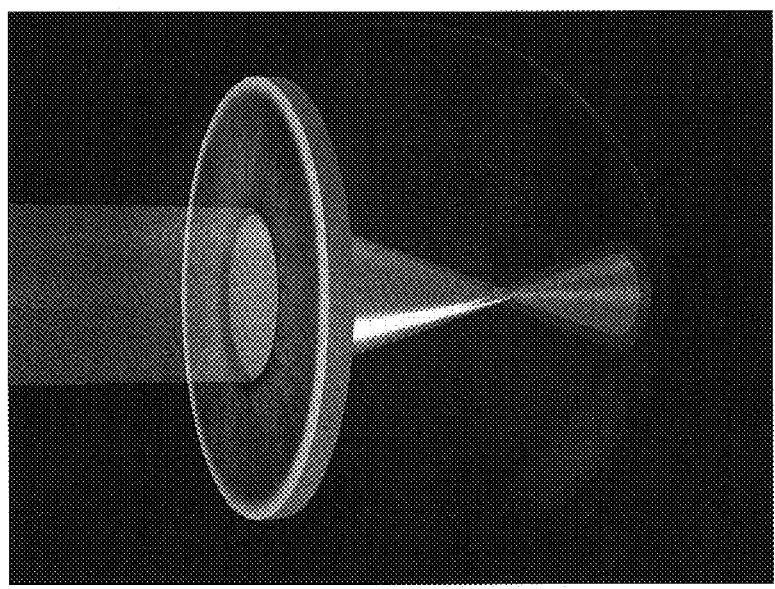
FIGS. 9A and 9B illustrate effects of chromatic aberration on a myopic eye point spread function.
Figure 9B:
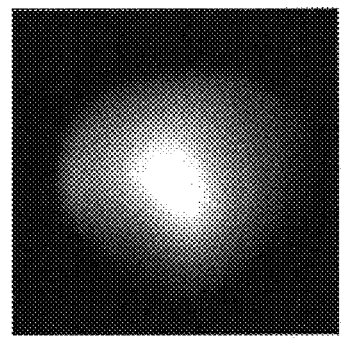

Referring now to FIG. 9A, the effect of chromatic aberrations on the myopic eye can also be understood. While a myopic eye generally focuses a light from a distant image at a location interior to the retina, the separation between the focal point and the retina varies with the light wavelength due to chromatic aberration effects. This can be seen in the point spread function illustrated in FIG. 9B.

Figure 10A:
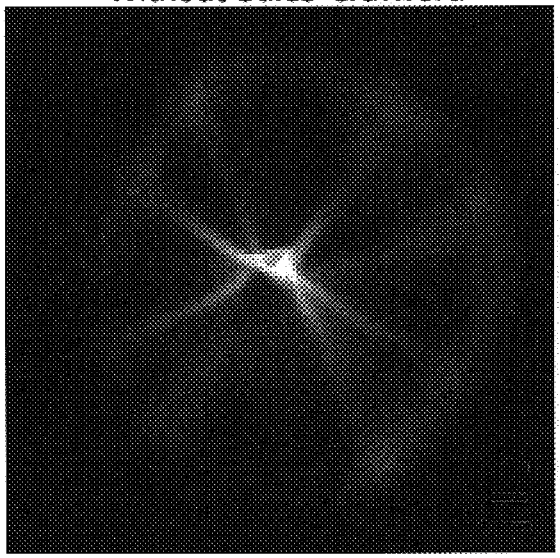
Figure 10B:
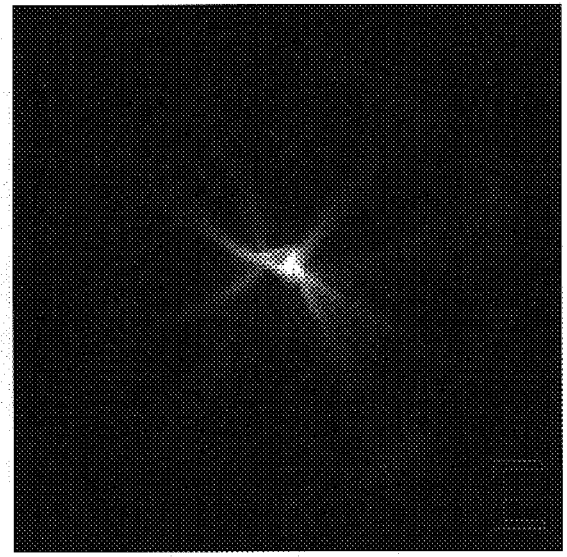

Referring now to FIGS. 10A and 10B, point spread functions calculated with (in FIG. 10B) and without (in FIG. 10A) effects of the Stiles-Crawford effect are illustrated for an eye with high spherical aberration (0.71 nm). An additional comparison of point spread functions in which Stiles-Crawford effect is omitted (FIG. 10C) and included (FIG. 10D) are also provided here for a myopic point spread function.

Calculation of the point spread function with the Stiles-Crawford effect and/or with the effects of multiple wavelengths of light are described in more detail in co-pending U.S. patent application Ser. No. 10/871,344, the full disclosure of which is incorporated herein by reference. Chromatic aberration at different wavelengths is also disclosed therein. More specifically, the point spread function (PSF) will typically be calculated based on the wavefront data. For example, a wavefront with aberrations can be denoted by $W(r, \theta)$. It is also possible to consider effects such as the polychromatic effect, the human eye's chromatic aberrations, the Stiles-Crawford effect, as well as the retinal spectral response function.

Considering these effects, the polychromatic PSF can be expressed as:

$$PSF = \sum_{\lambda} R(\lambda) \left| FFT\left(P_{sc}(r) \exp\left[-j\frac{2\pi}{\lambda}[W(r,\theta) + \alpha D(\lambda)]\right]\right)\right|$$

where $R(\lambda)$ is the retina spectral response function and can be approximated to $$R(\lambda) = e^{-300(\lambda - \lambda_0)^2}$$

and $P_{sc}(r)$ is the pupil apodization function (Stiles-Crawford effect) and can be written as $$P_{sc}(r) = 10^{-\rho\frac{r^2}{R^2}}$$

and $D(\lambda)$ is chromatic aberration at wavelength $\lambda$ and can be close to $$D(\lambda) = -21.587 + 92.87\lambda - 134.98\lambda^2 + 67.407\lambda^3$$

and the central wavelength $\lambda_0$ can be taken as 0.55 μm (as all wavelength units in the above formulae can be in μm). The pupil apodization strength parameter $\rho$ can be taken as 0.06. $\alpha$ can represent the conversion factor from diopter to optical path difference (OPD). FFT can denote a fast Fourier transform and |*| denotes the module of a complex number.

In implementing the polychromatic wavelengths, it has been found that 7 wavelengths at 0.40, 0.45, 0.50, 0.55, 0.60, 0.65, and 0.70 μm, respectively, give adequate approximation for the entire white-light spectra.

Figure 11A:
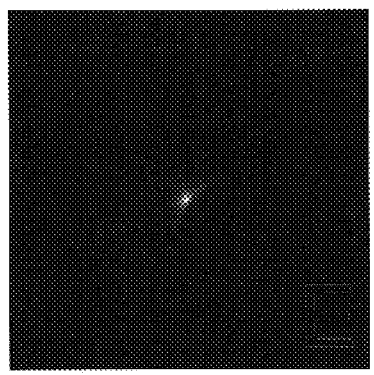
FIGS. 11A-11F illustrate effects of non-linear retinal response on point spread functions.
Figure 11C:
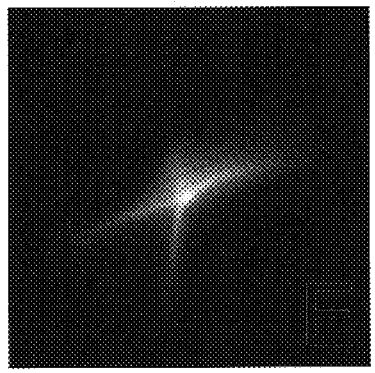
Figure 11E:
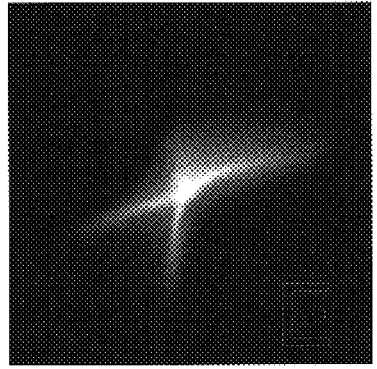
Figure 11B:
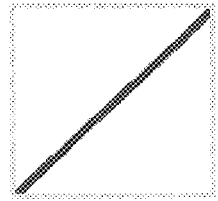
Figure 11D:
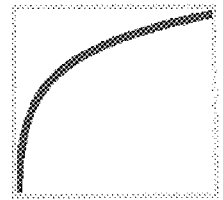
Figure 11F:
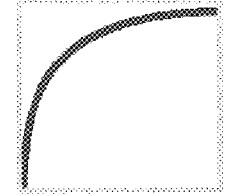

Referring now to FIGS. 11A through 11F, another factor which affects perceived point spread functions is the non-linear response of the retina. As illustrated in FIG. 11A, a point spread function calculated with an assumed linear response (as illustrated in FIG. 11B) may, at least in some cases, significantly misrepresent the perceived visual effects of aberrations. By altering the point spread function calculation so as to include a logarithmic response (as illustrated in FIG. 11D), correlation with perceived aberrations effects may be improved. Such correlations may, in at least some cases, be further improved by incorporating both a logarithmic response and saturation of the retina to light energy as illustrated in FIGS. 11E and 11F.

Figure 12:
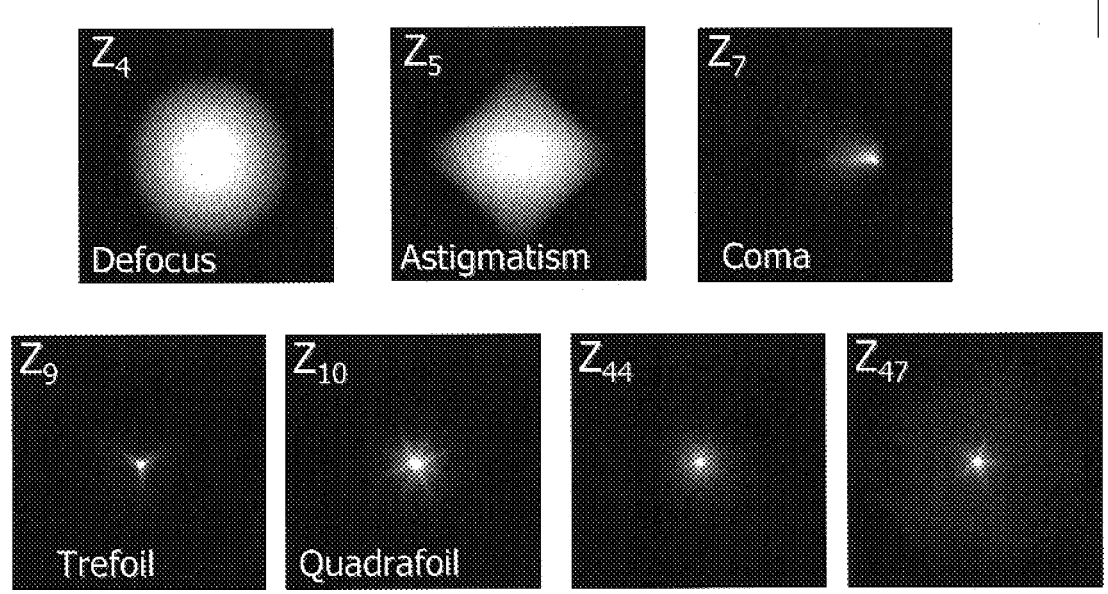
FIG. 12 illustrates point spread functions of a selected set of traditional Zernike Aberrations.
Figure 13:
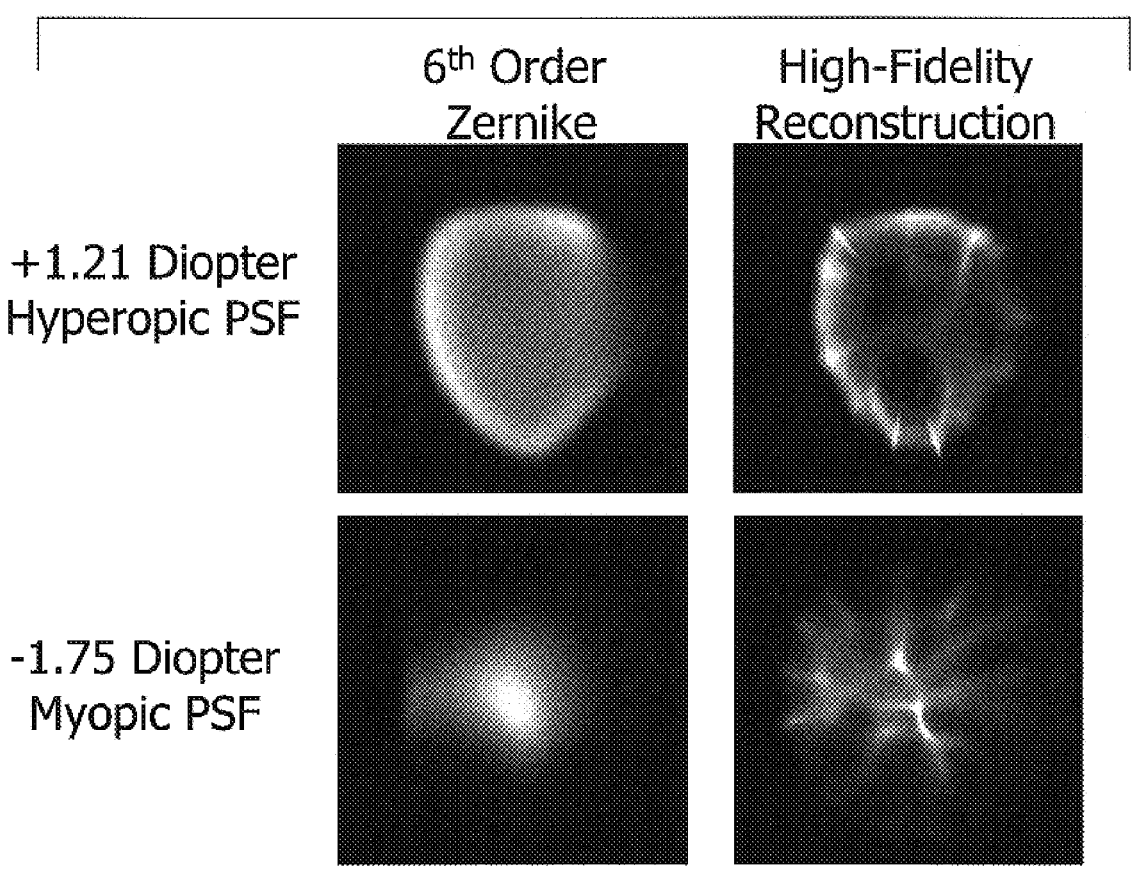
FIGS. 13 and 14 illustrates how the reconstruction (here a 6th order Zernike reconstruction and a high-fidelity Fourier reconstruction) can effect the point spread function.
Figure 14:
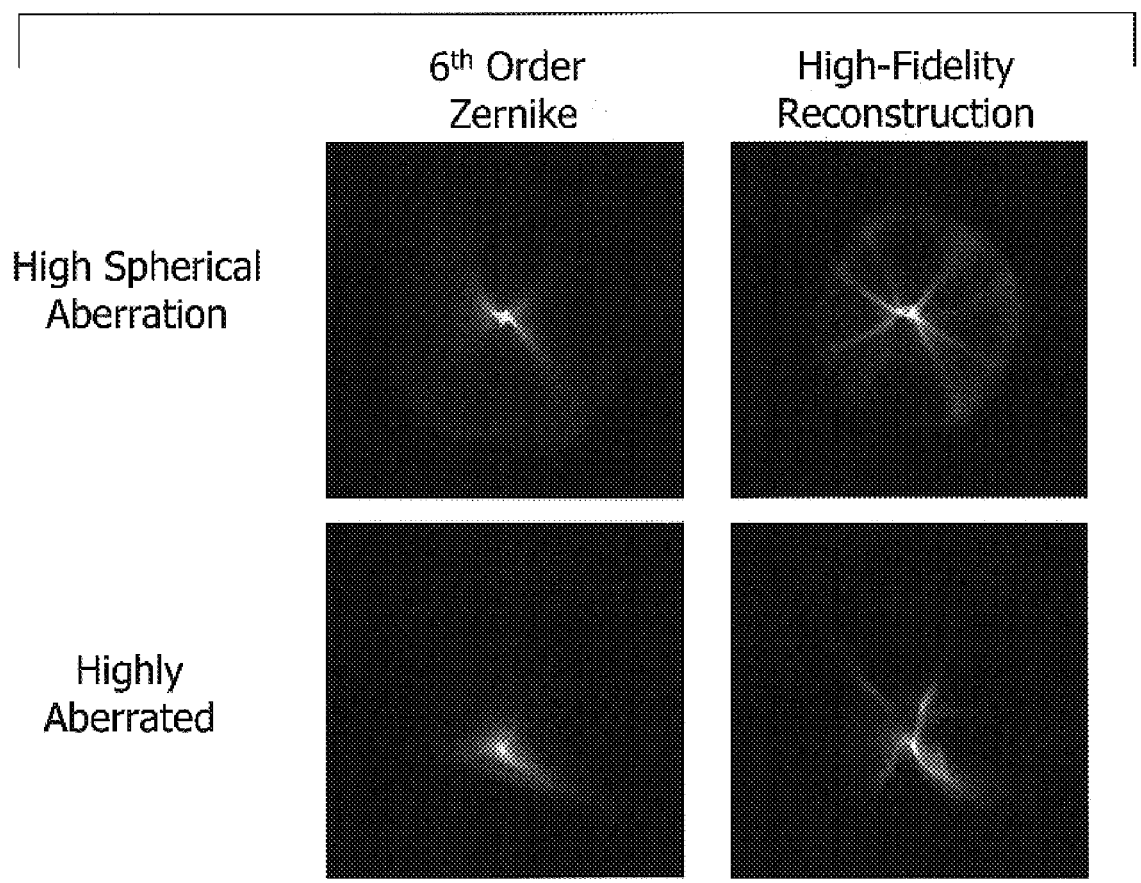

Referring to FIG. 12, a subset of the traditional Zernike aberrations are illustrated. Unfortunately, as noted by Michael K. Smolek and Stephen D. Klyce in their article entitled "Zernike Polynomial Fitting Fails to Represent All Visually Significant Corneal Aberrations," [Invest Ophthalmol Vis Sci, (11/2003) 44(11) 4676-4681 DOI:101167/IOVS.03-0190], known Zernike fitting methods are inexact. These known Zernike fitting methods also do not fully capture important information about wavefront error operations that influence visual acuity. Hence, although Zernike polynomial wavefront reconstructions from aberration data are quite popular and can provide significant benefits for many patients, these known Zernike reconstructions do affect the point spread function in ways that may limit the accuracy of these representations of the visual perception of the patient. For example, FIG. 13 illustrates a comparison between point spread functions based on 6th order Zernike polynomial reconstructions to more high fidelity reconstructions. The exemplary highly fidelity reconstructions comprise high resolution Fourier reconstructions. Significant differences in the point spread functions can be seen for both the 1.21 diopter hyperopic point spread function and the −1.75 diopter myopic point spread function. Differences can also be seen in a point spread function for a patient having high spherical aberration and a highly aberrated patient as illustrated in FIG. 14. In FIG. 14, the bottom row shows a 6th order wavefront reconstruction-based point spread function of a high aberrated eye (RMS=to 0.89 nm). The image on the right was calculated from the same wavefront, but using a high fidelity Fourier reconstruction. The substantial differences between the images implies that 6th order Zernike reconstruction is not sufficient to generate a fully accurate point spread function.

Figure 15:
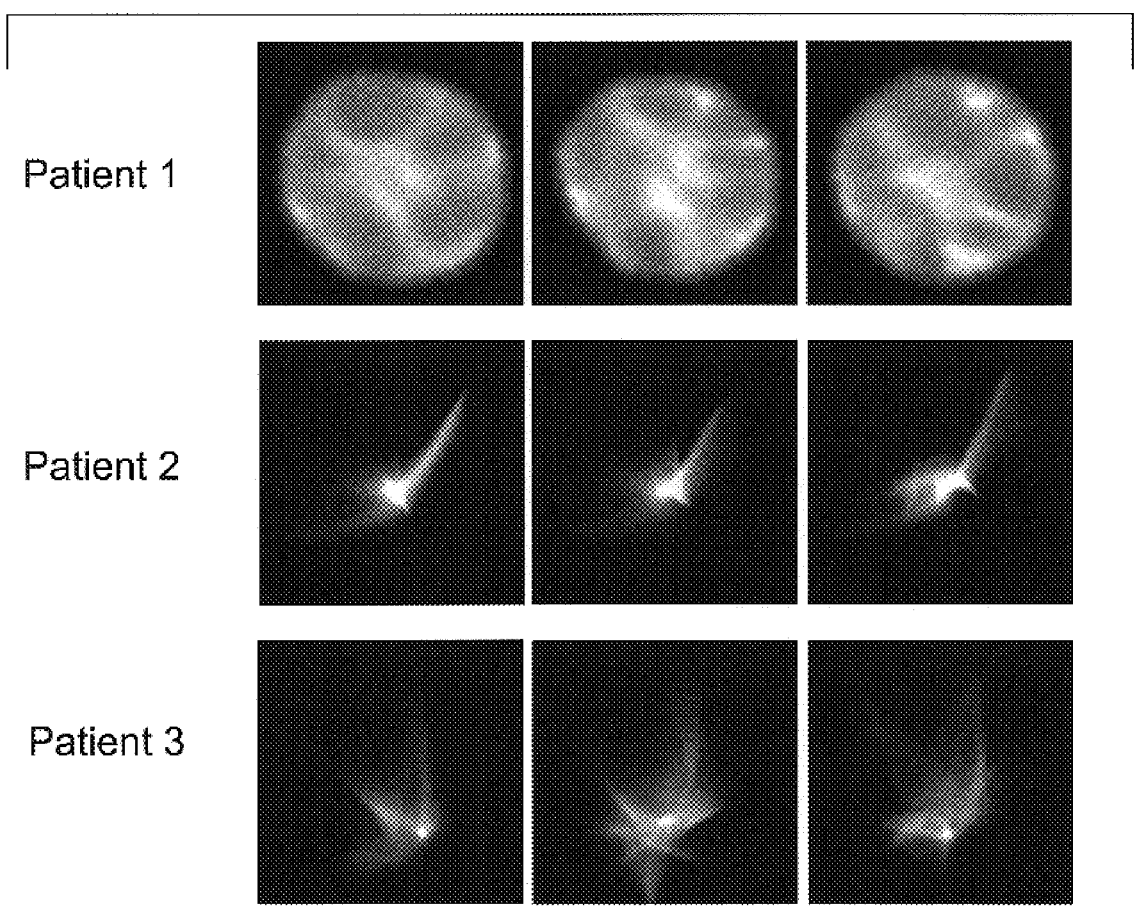
FIGS. 15-17 show repeatability of point spread functions for different patients.
Figure 16:
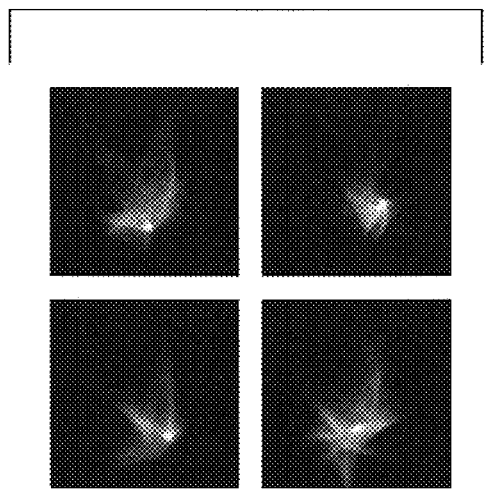
Figure 17:
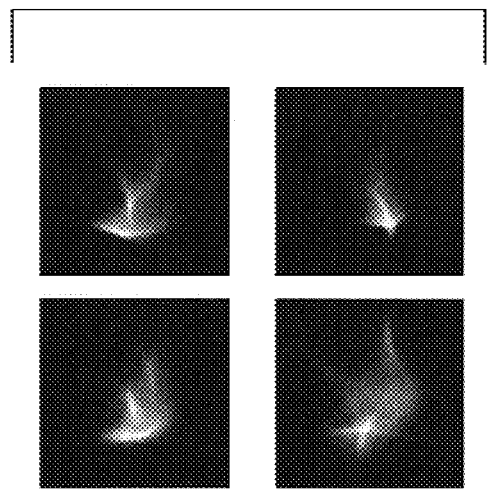

Referring now to FIG. 15, repeatability of point spread functions for different patients (patient 1, patient 2, and patient 3) having different aberrations are illustrated. FIGS. 16 and 17 also graphically illustrate the repeatability of point spread functions.

Figure 18A:
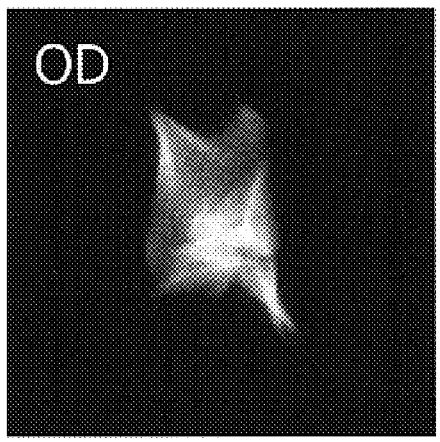
FIG. 18A-18D illustrate a point spread function test in which a wavefront-derived point spread functions are compared to patient perceived and drawn documentation of their visual perception.
Figure 18B:
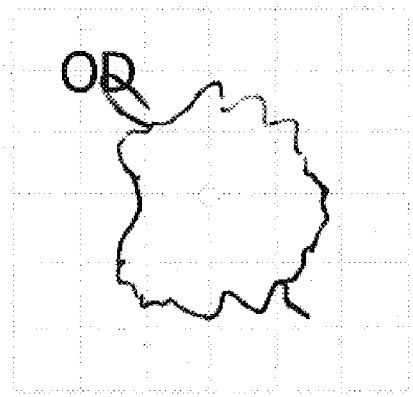
Figure 18C:
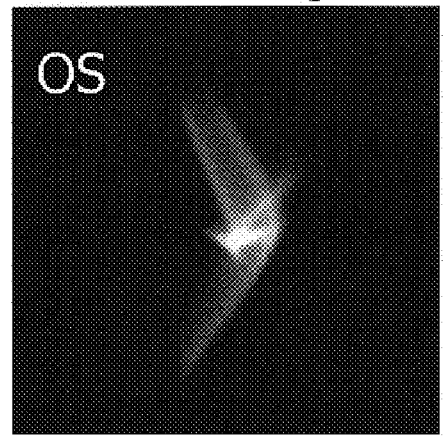
Figure 18D:
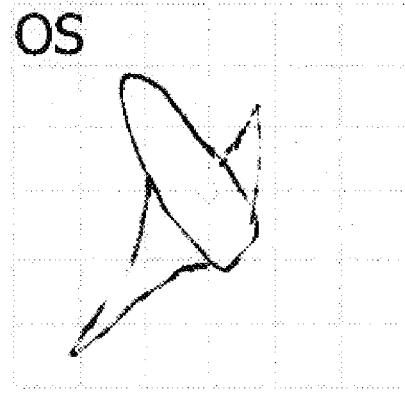

Referring now to FIGS. 18A through 18D, a patient with significant aberration (four days after a photorefractive keratectomy ("PRK") procedure during re-epithelialization) was measured on a WaveScan WaveFront® aberration sensing system. The data was used to calculate a point spread function for the right eye ("OD") as illustrated in FIG. 18A, and for the left ("OS") as illustrated in FIG. 18C. The patient was shown a light source set against a ruled background and was asked to draw the image as seen with each eye. For the right eye OD, the patient drew the sketch shown in FIG. 18B. For the left eye OS, the patient drew the sketch shown in FIG. 18D. The close match in scale and shape of each of these figures with the associated calculated perceived point spread function indicates that the perceived point spread function is predicting the patient's visual perception. Hence, this provides an example of a point spread function testing protocol: when a patient's drawings of a small light source sufficiently resemble the wavefront aberration-based point spread functions in both scale and features, such results indicate that point spread functions can provide validation to the patient of his or her visual perception, and also indicate that visual perception may be used to validate the calculated point spread function and aberration measurements.

Figure 19:
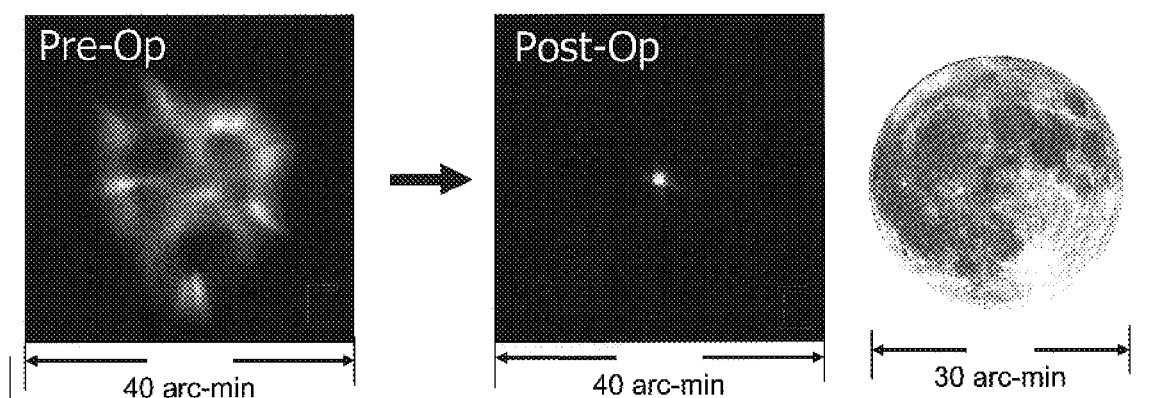
FIGS. 19 and 20 illustrate point spread functions of a patient before and after LASIK.

Referring now to FIG. 19, a point spread function showing aberrations of a patient's eye prior to LASIK was shown to be improved significantly by comparison to a point spread function calculated for the same patient after the LASIK procedure. Both point spread functions are illustrated with a common scale, and an illustration of the moon at that scale is provided for comparison purposes. Both the pre-LASIK operation and post-LASIK operation point spread functions are self normalized in FIG. 19.

Figure 20:
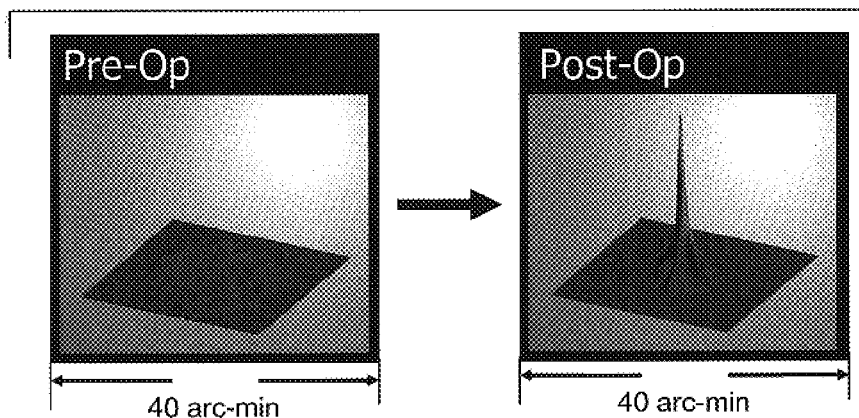

Referring now to FIG. 20, an alternative representation of the pre-LASIK operation and the post-LASIK operation point spread functions of FIG. 19 are illustrated. The pre-LASIK operation point spread function of FIG. 20 is normalized to the post-LASIK operation point spread function, which is again self normalized.

Along with direct viewing and analysis of the point spread function, the point spread functions described herein may also be used for convolution of images, thereby providing an objective graphical display corresponding to the patient's visual perception. As more fully described in patent application Ser. No. 10/871,344, the disclosure of which is incorporated herein by reference, appropriate test image convolution may be used to gauge visual acuity on an objective basis.

Figure 21:
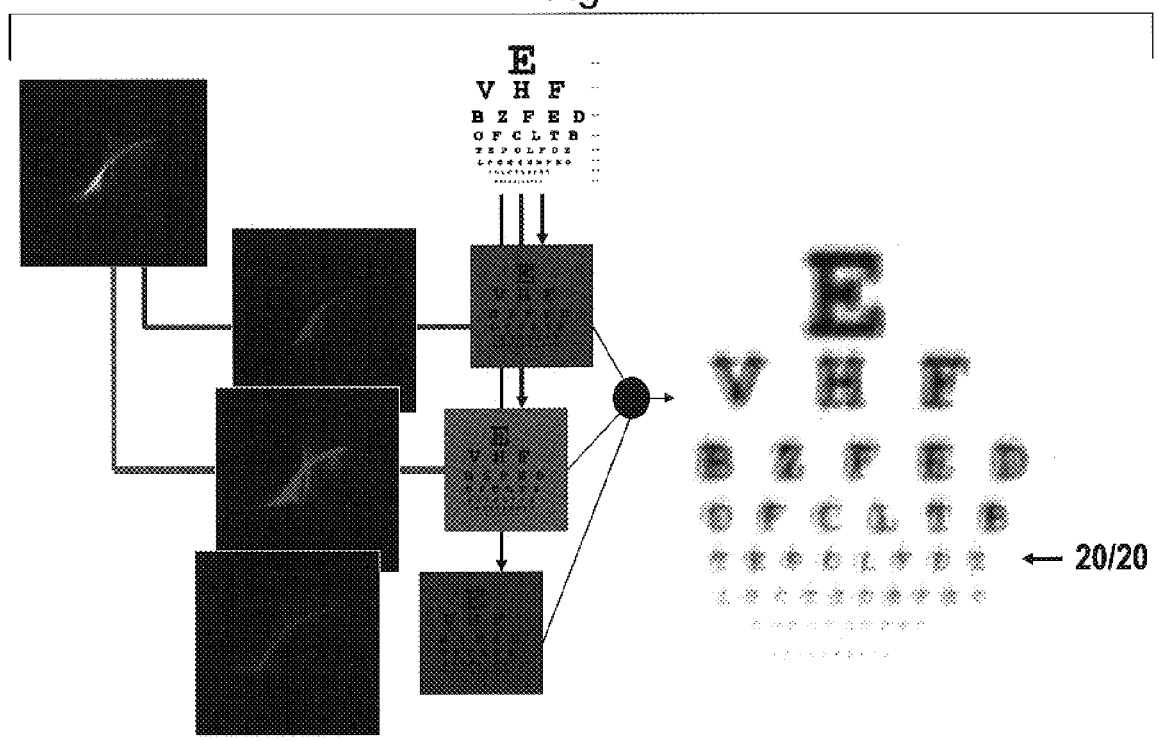
Figure 23:
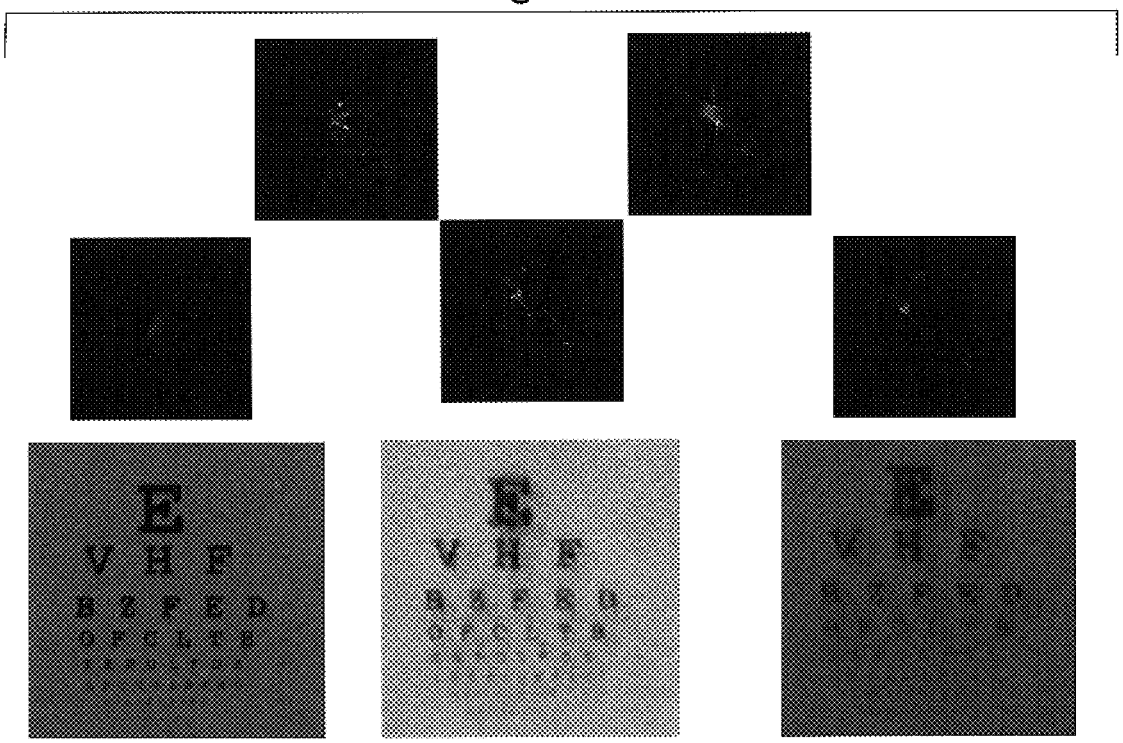

As illustrated in FIG. 21, the different light wavelengths which may be combined to illustrate light point spread function may be convolved with a Snellen or other appropriate test image to provide an indication of wavelength-specific vision, and/or the different color convolved test images may be combined to illustrate a white light (or other combined light) test image corresponding to what a patient perceives. FIG. 22A illustrates a point spread function for a white light or solar spectrum light source, and FIG. 22E illustrates a corresponding white light Snellen eye chart convolved using the point spread function of FIG. 22A. Similarly, FIG. 22F illustrates a blue light 400 nm Snellen eye chart convolved from a blue emitting diode (LED) point spread function of FIG. 22B. FIG. 22G illustrates a similar test image convolved using the red LED 665 nm light source point spread function of FIG. 22C, while FIG. 22D shows a yellow or Sodium light 590 nm point spread function with the associated convolved test image being shown in FIG. 22H. As illustrated in FIG. 23, the point spread functions (and associated convolved test images) may also be combined in different manners, for example, so as to analyze light sources which are formed from different combinations of desired colors.

Figure 26:
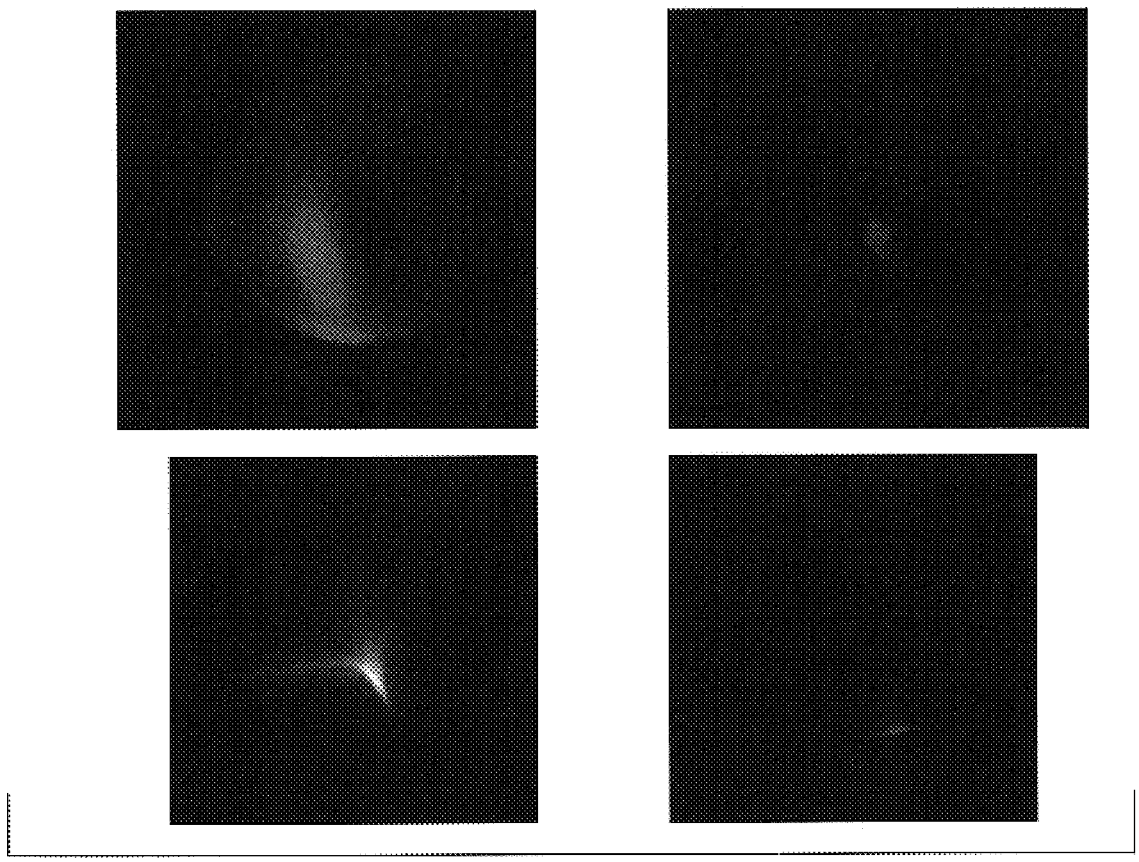

As indicated by the above, using the model eyes described herein allows different light spectra to be used in generating the point spread function. While a white light solar spectrum is shown in many of the illustrations herein, point spread functions have also been tested using the spectra of alternative light sources including halogen lights, tungsten lights, commercial light emitting diodes, and commercial street lighting. The results show that a patient's point spread function can be significantly affected by the source light spectrum. A patient with a good point spread function in white light may have a poor point spread function if looking at a red light emitting diode. Each point spread function can be convolved with an image of a traditional Snellen eye chart or other desired image so as to estimate the patient's visual acuity under different lighting conditions. Hence, point spread function with different light spectra may be derived, depending on what light we wish to model. For example, FIGS. 24A and 24B illustrate images generated using point spread functions of halogen and Xenon high intensity discharge ("HID") lights having color temperatures of 3,000K and 5,200K, respectively. The images shown in FIGS. 24A and 24B graphically illustrate what the patient might see as a result of BMW lights pointed toward the patient at 100 meters distance from the patient, which represents about 1.5 seconds away from the patient at freeway speeds. Similar illustrations are shown in FIGS. 25A and 25B. FIG. 26 illustrates additional color point spread function illustrations.

Referring now to FIGS. 27A through 27M, a point spread function may be calculated by simulating light from throughout the entire pupil. However, by using a geometric eye model (see, for example, FIG. 36), a one-to-many relationship can be established between each point in the patient's wavefront and the components of the point spread function. In one mode of the model, the user is presented with an eye image of the patient's point spread function. The user can point a cursor at a portion of the pupil and immediately see which part of the point spread function is generated by the highlighted portion of the wavefront. This technique may be useful when the eye is highly aberrated. In fact, it is possible to isolate features in the point spread function and relate the cause of a particular flare or ghost to a specific area on the eye.

As illustrated in FIG. 27A, the light from throughout substantially an entire pupil may be used to calculate a full point spread function such as that shown in FIG. 27B. However, by simulating a light from only a small portion of the pupil such as that illustrated in FIG. 27C, the associated portion of the point spread function may be identified, as shown in FIG. 28D. The full pupil light throughout the area highlighted in FIG. 27E produces the full point spread function shown in FIG. 27F, while the portion of the pupil highlighted in FIG. 27G is associated with the partial point spread function illustrated in FIG. 27H. The full versus partial point spread function comparison available by comparing FIGS. 27A through 27D are those of a hyperope, and the full and partial point spread functions of FIGS. 27E through 27H are from a myope.

Figure 27M:
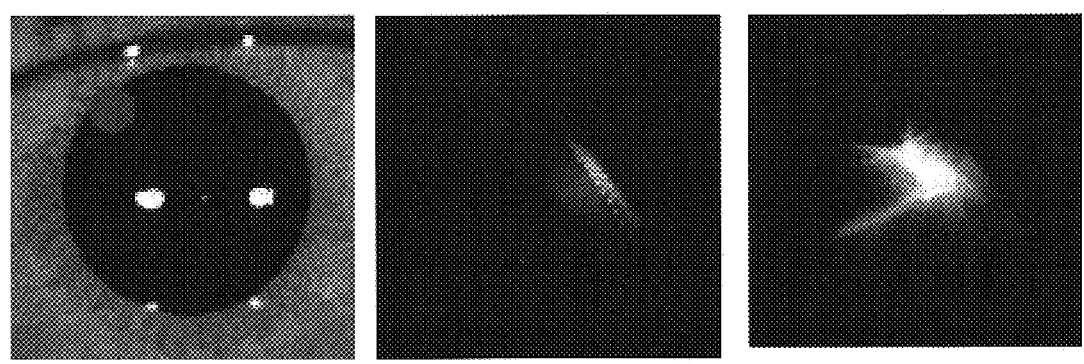

Referring now to a full point spread function over an entire pupil as illustrated in FIGS. 27I and 27J, these illustrations are for an emmetrope with high order aberrations. When a partial point spread function FIG. 27L is taken for a region of the eye illustrated in 27K which is outside the pupil, the partial point spread function establishes (as expected) that this region of the eye does not contribute to the point spread function of the patient. For completeness, a partial point spread function of another patient is illustrated in FIG. 27M along with the associated portion of the pupil.

Figure 28A:
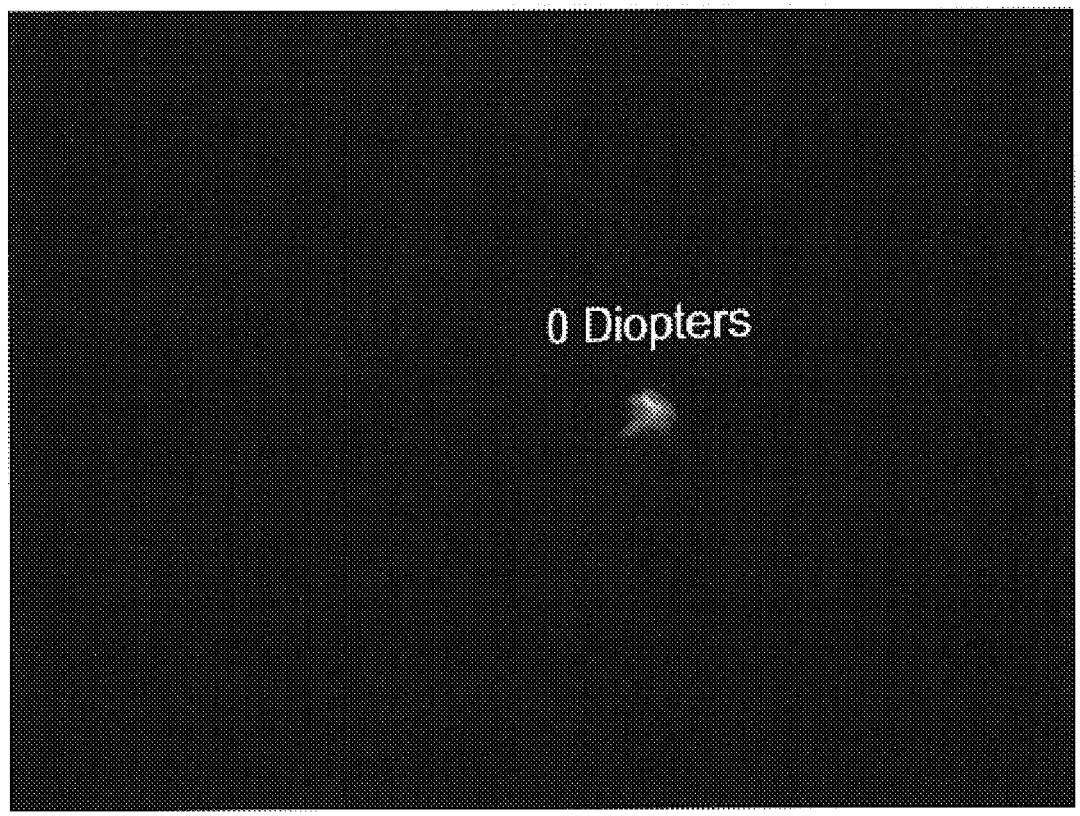
FIGS. 28A-28C illustrate a volumetric point spread function and a method for generating the volumetric point spread function.
Figure 28B:
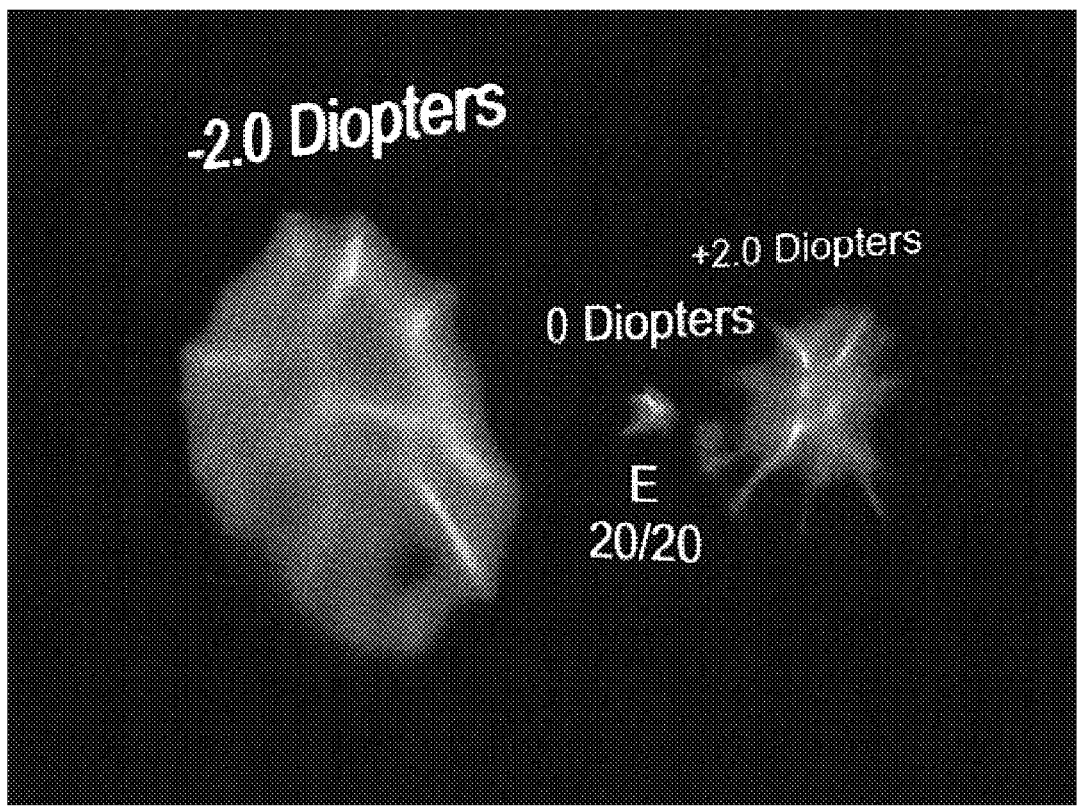

Referring briefly again to FIG. 4, the eye is a three-dimensional structure, and an appropriate model of the eye should also be three-dimensional. For example, a point spread function should ideally be more than just an image. Referring now to FIG. 28A, a point spread function is illustrated at a retinal plane. The eye, however, does not only view objects at a fixed distance (far distance viewing in this example). In fact, because the optics of the eye (particularly the lens of the pupil) may adjust to viewing at different distances, and because the eye will often have at least some myopia or hyperopia in at least some viewing conditions, it may produce images in front of and/or behind the retina. Understanding the effects at image planes other than the retina may therefore, give a fuller indication of the overall visual performance of the eye. Toward that end, FIG. 28B illustrates point spread functions at the retinal plane, at two diopters anterior to the retinal plane, and at two diopters posterior to the retinal plane.

Figure 28C:
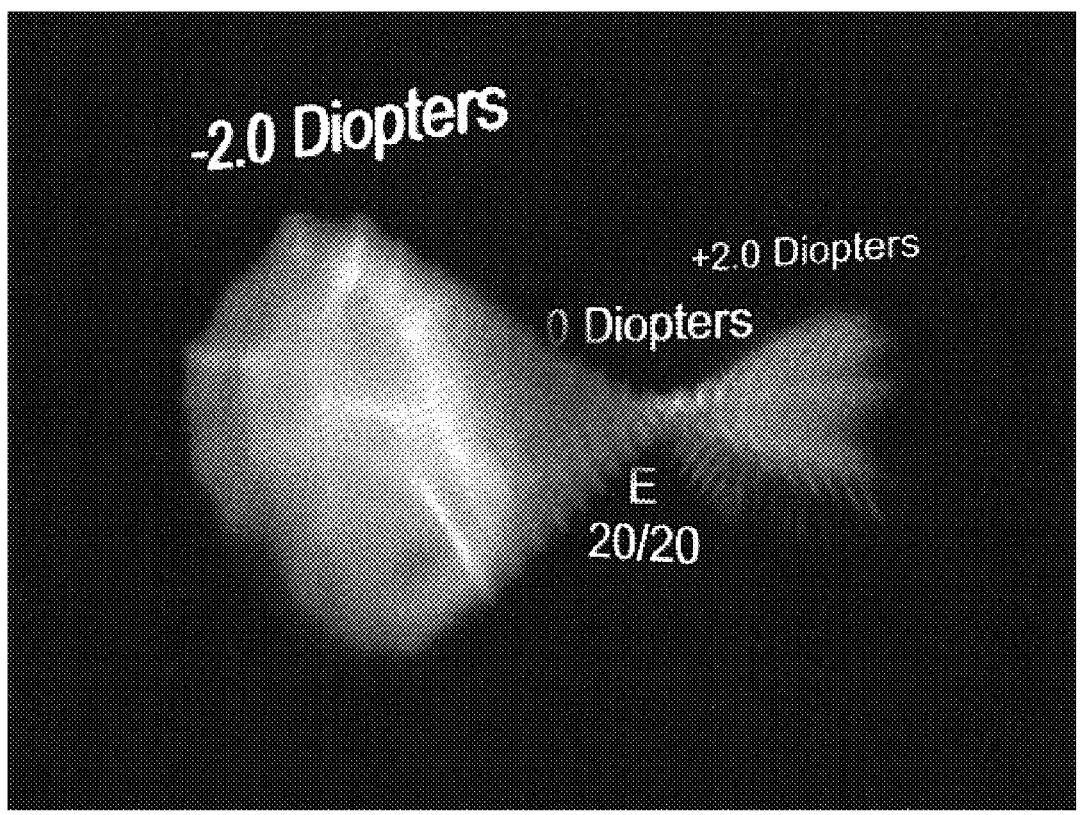

As viewing may occur at a range of distances between those associated with these point spread functions, FIG. 28C illustrates a volumetric point spread function. In the illustrations of FIGS. 28B and 28C, the discreet point spread functions at −2.0 diopters are in front of the retinal plane, while the point spread functions at +2.0 diopters are behind the retinal plane. The point spread function illustrated for 0 diopters is at the retinal plane, and the Snellen "E" associated with 20/20 visual acuity is again provided for reference.

The volumetric point spread function of FIG. 28C illustrates point spread functions at a plurality of separation distances from the cornea, pupil, and other anterior optical components of the eye and the point spread function reference plane. Preferably, the volumetric point spread function will include at least an anterior-most and posterior-most point spread function, along with at least one intermediate point spread function, often disposed at or adjacent the retinal location. In many embodiments, a plurality of additional intermediate point spread functions will also be derived and/or displayed with at least one point spread function being disposed between a retinal plane point spread function and each of the anterior-most and posterior-most point spread functions, preferably with a plurality of such intermediate point spread functions disposed therebetween In some embodiments, the volumetric point spread function may be derived and illustrated as a continuous function throughout a range of distances, and the point spread function range will often encompass and/or be adjacent to the retina.

Figure 29:
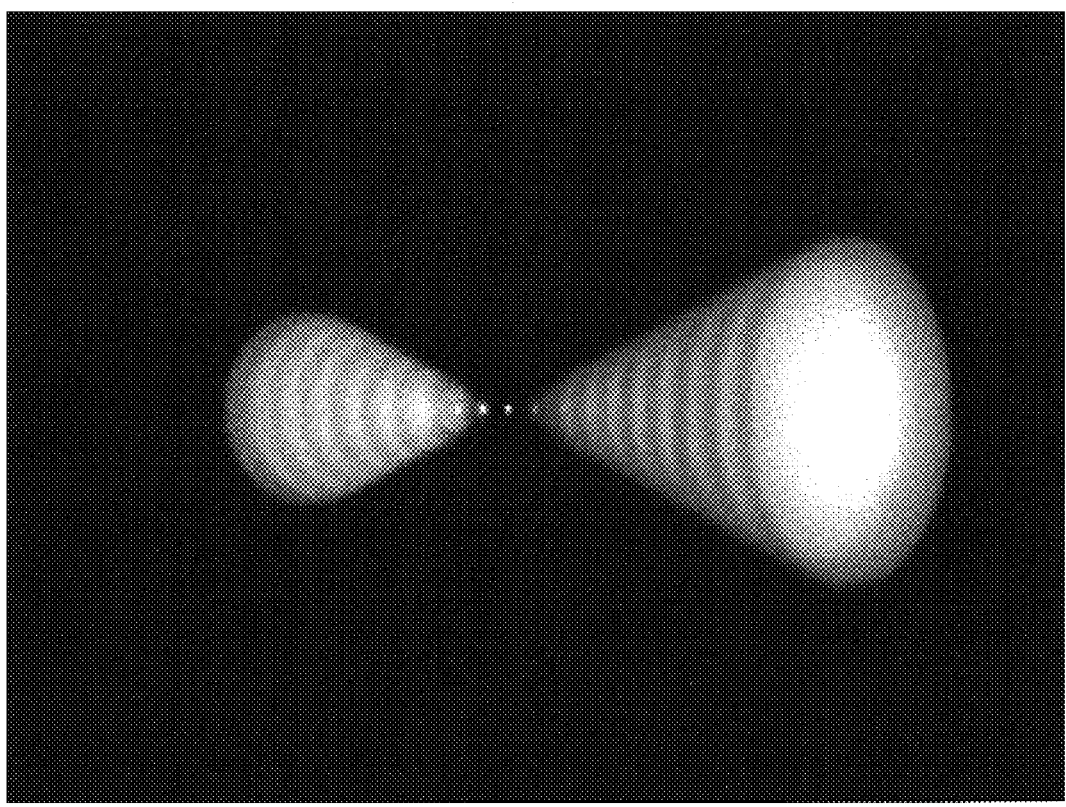
FIG. 29 illustrates an aberration free volumetric point spread function.
Figure 30:
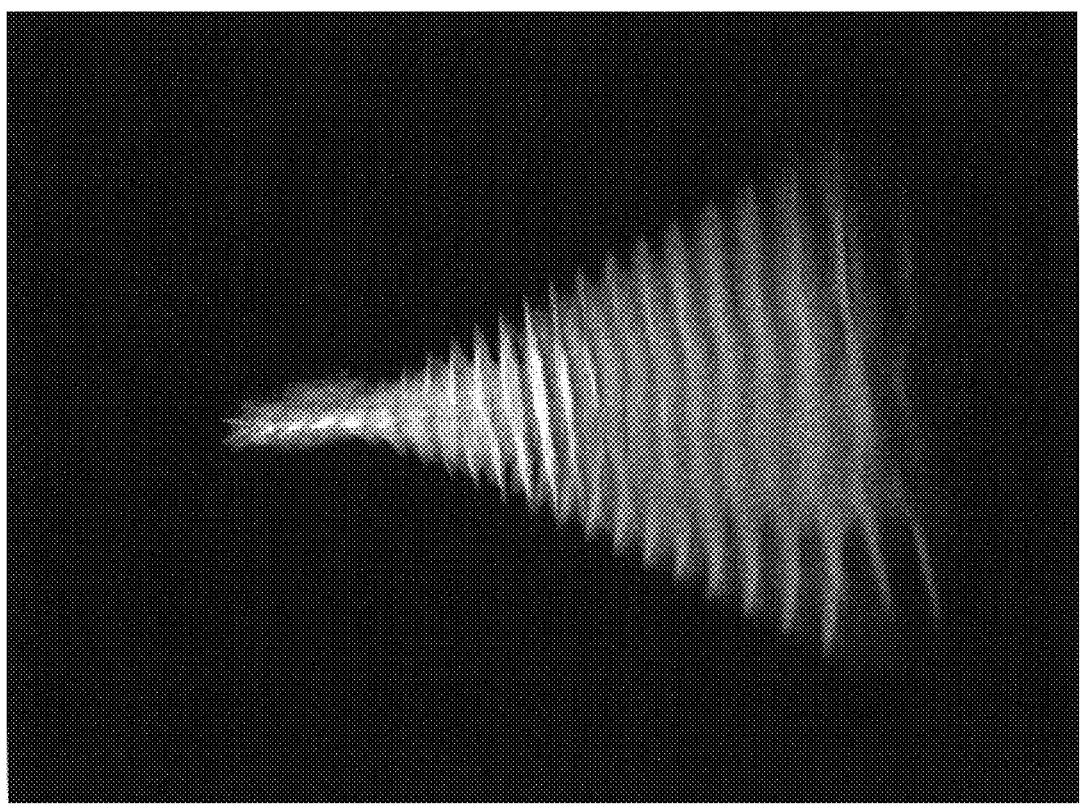
FIGS. 30 and 31 illustrate volumetric point spread functions for eyes having different types of refractive defects.
Figure 31:
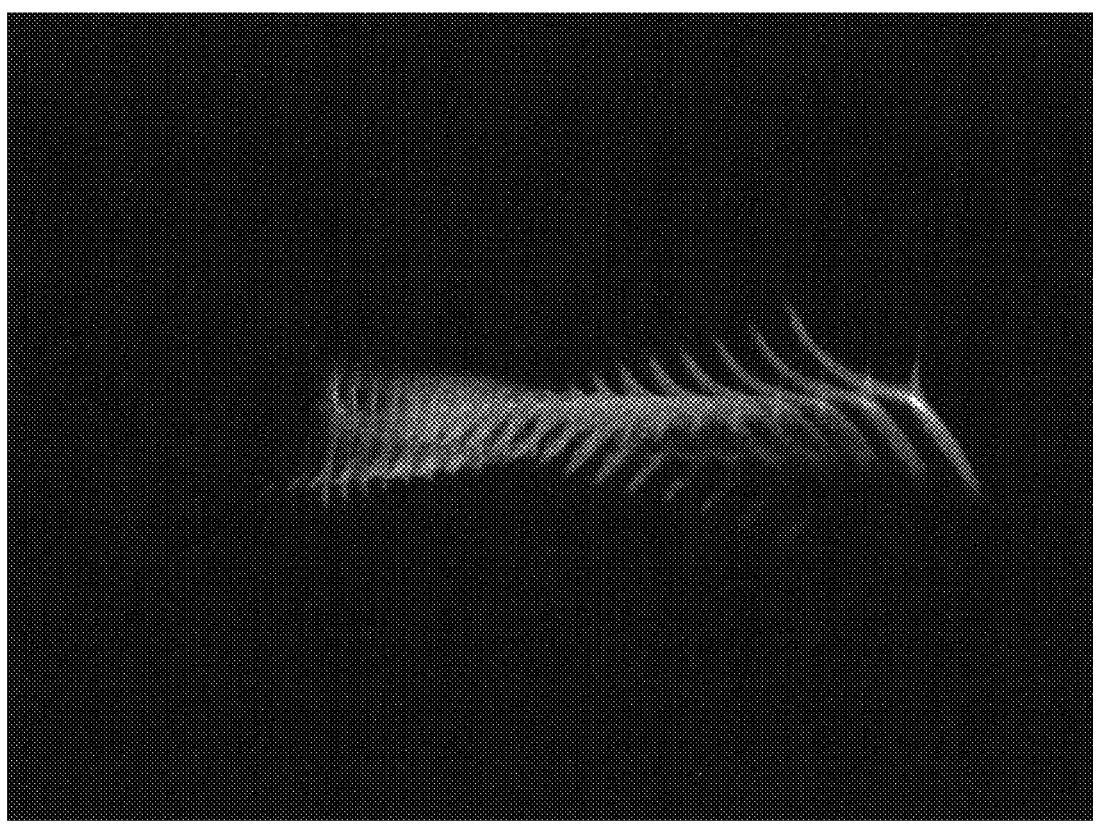

As can be understood by a comparison of FIGS. 9A and 28C, wavelength and/or chromatic aberration effects may play a part in the volumetric point spread function, and are well illustrated thereby. A volumetric point spread function for an aberration free eye is shown in FIG. 29. A volumetric point spread function for an eye having a mixed astigmatism is FIG. 30. A volumetric point spread function for a highly aberrated eye is shown in FIG. 31.

Figure 32:
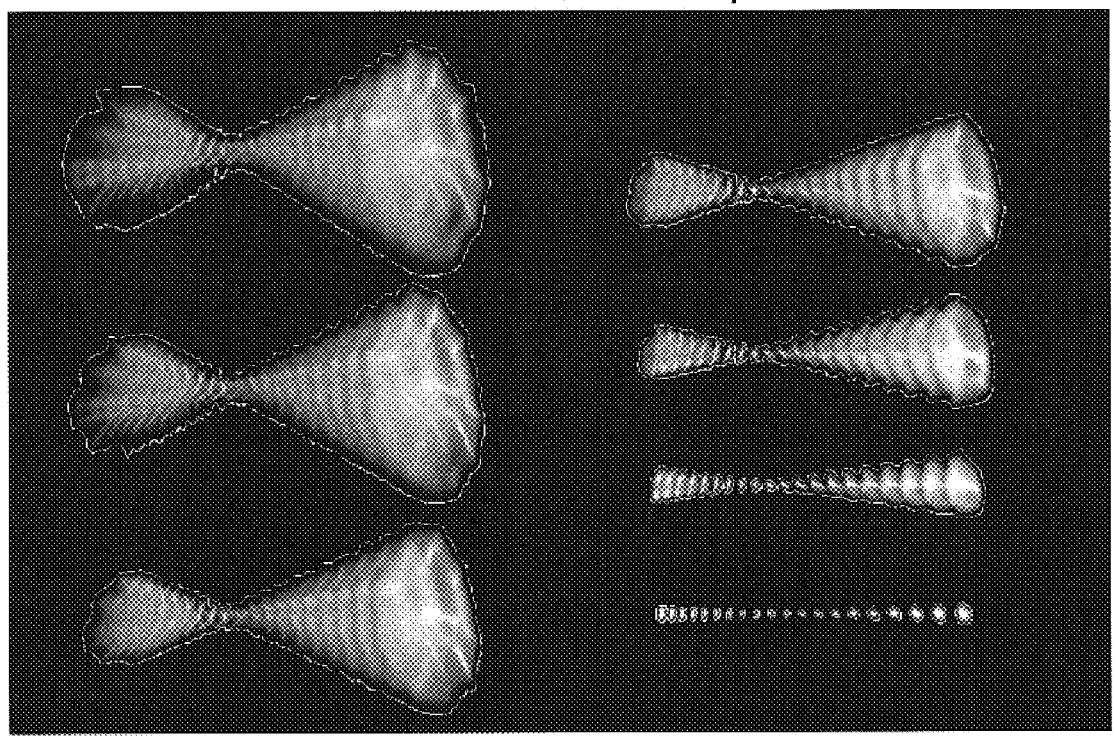
FIG. 32 illustrates volumetric point spread function as a function of pupil size.
Figure 33:
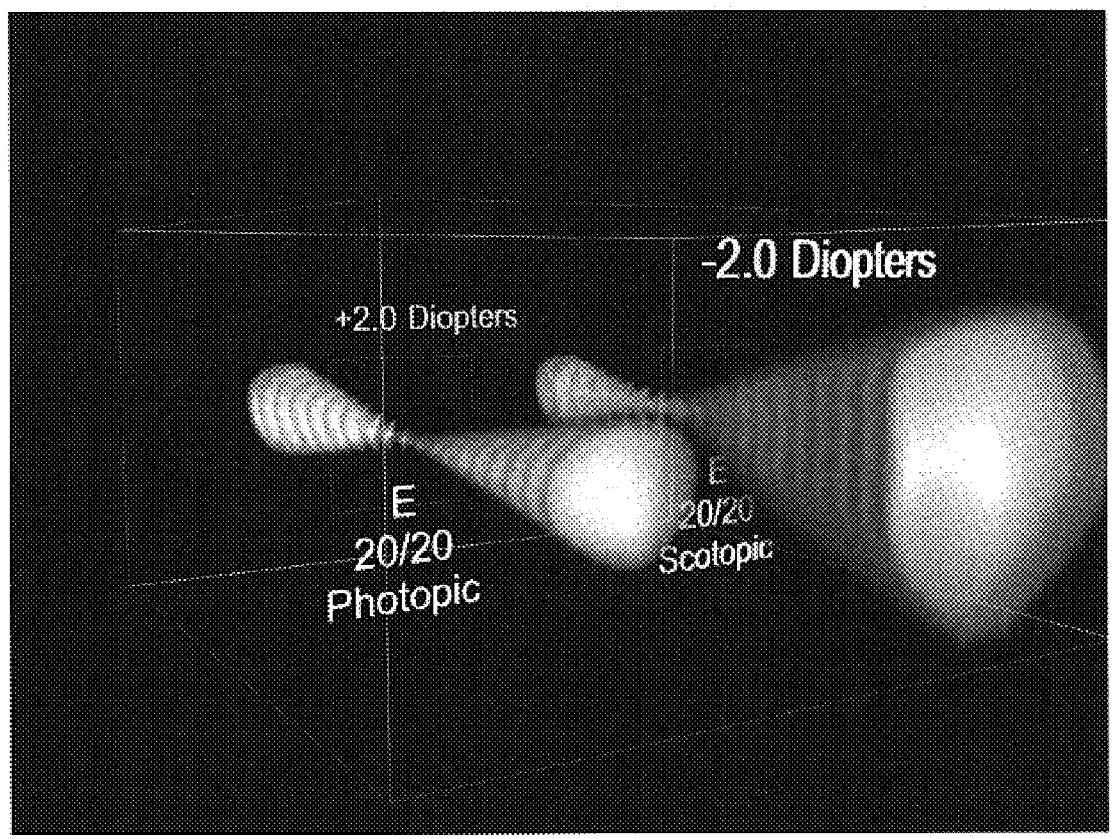
FIGS. 33 and 33A illustrate volumetric point spread functions under photopic and scotopic conditions.
Figure 33A:
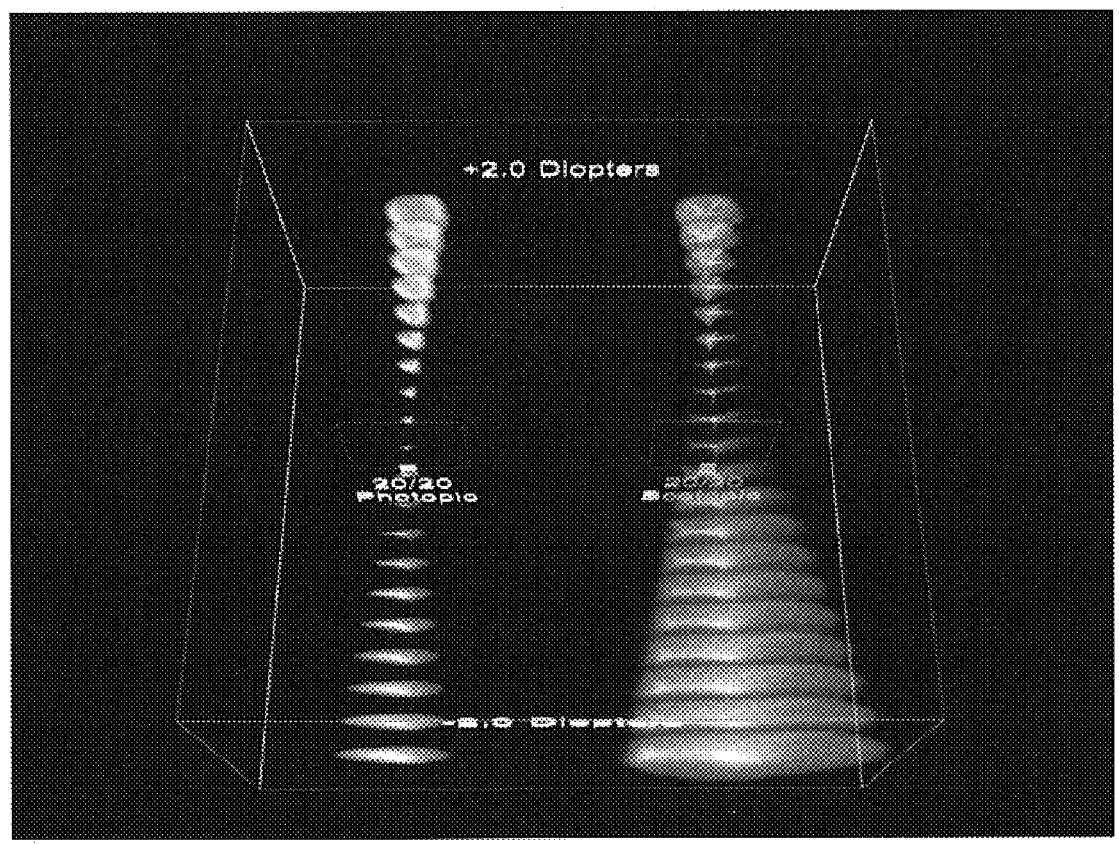

As noted above, and as described in more detail in U.S. patent application Ser. No. 10/738,358, filed on Dec. 5, 2003, and entitled "Presbyopia Correction Using Patient Data", the full disclosure of which is incorporated herein by reference, the size of the pupil changes with changes in both brightness (ambient and/or of the viewing image) and with changes in viewing distances. As illustrated in FIG. 32, changes in the size of the pupil can have a significant effect on the volumetric point spread function. FIG. 33 shows a comparison of the volumetric point spread functions under photopic and scotopic conditions. The wavefront here is of an emmetropic patient, and the calculated volumetric point spread function for photopic or daytime conditions was calculated for a peak wavelength of 555 nm and a pupil diameter of 4.1 mm, with Stiles-Crawford effect being modeled. The scotopic volumetric point spread function for nighttime viewing conditions was calculated with a peak wavelength of 507 nm and a pupil diameter of 6.5 mm, without any Stiles-Crawford effect. The wavelength selections can be understood with reference to FIG. 6A, as explained above. Another view of the volumetric point spread functions under photopic and scotopic conditions is shown in FIG. 33A.

In general, the point spread function captures an image at the patient's retina. By extending the model using the volumetric point spread function, it is possible to calculate a point spread function at theoretical locations before and beyond the retina. By arranging a series of these images into a three-dimensional array, the point spread function can be viewed as an extended three-dimensional structure encompassed by the term volumetric point spread function as that term is used herein. The volumetric point spread function can be used to study a patient's depth of focus, and to see the interaction of the patient's defocus and high-order aberrations.

Figure 34A:
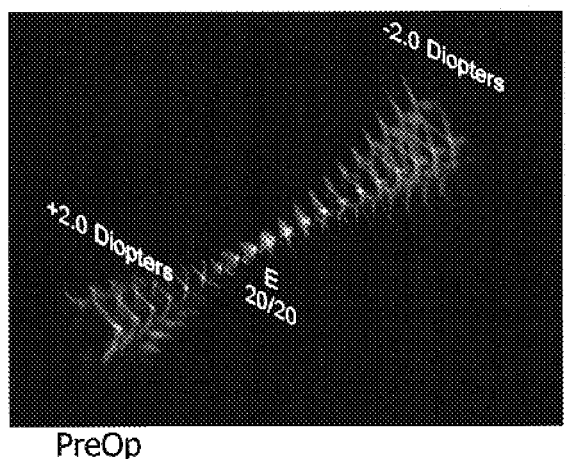
FIGS. 34A-34C illustrate volumetric point spread functions of a patient before and after treatment for presbyopia.
Figure 34B:
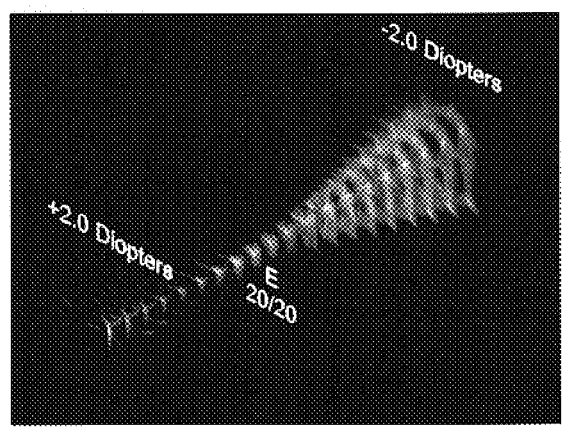

Referring now to FIGS. 34A and 34B, the volumetric point spread function can be used to analyze depth of focus preoperatively (as shown in FIG. 34A) and post operatively (as shown in FIG. 34B) for a patient participating in a presbyopia refractive ablation clinical trial. The volumetric point spread function clearly shows that the patient's depth of focus has increased to include a larger reading range, in this case up to two diopters.

Figure 34C:
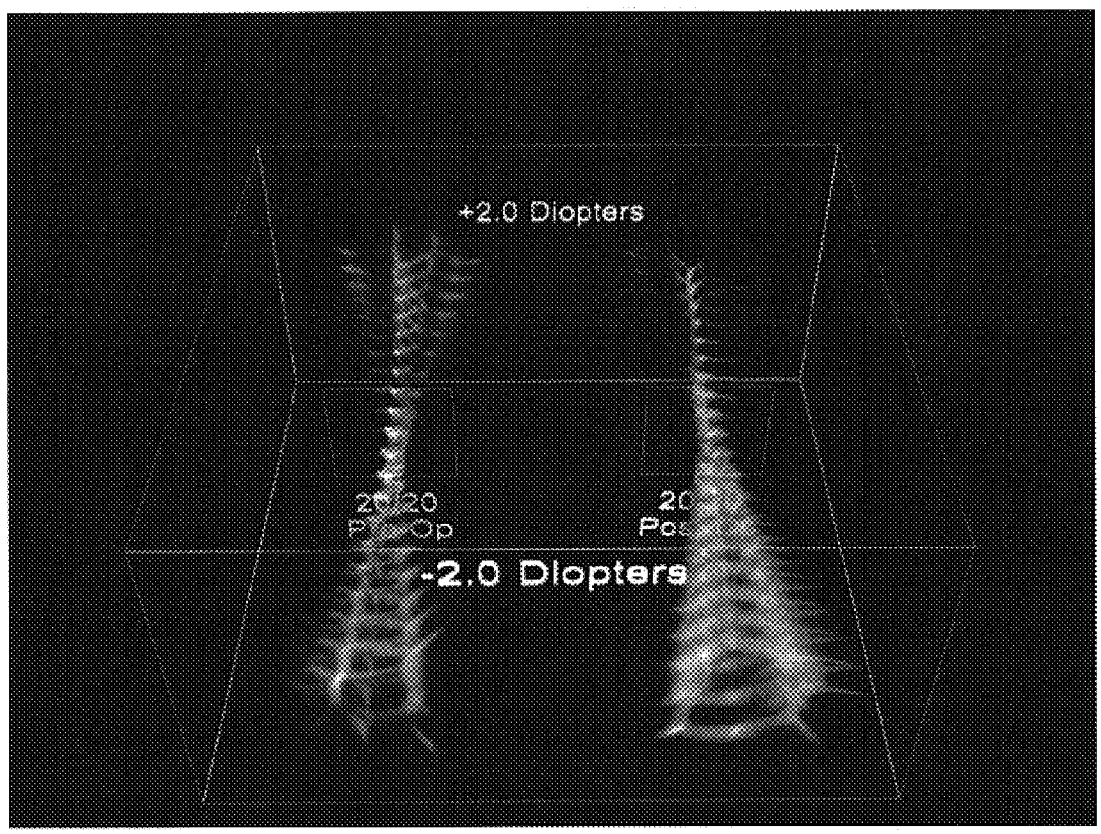

The volumetric point spread functions of FIGS. 34A and 34B are generated by calculating the point spread function at a plurality of locations, preferably at many locations, throughout a focus range, and graphically and/or computationally arranging the calculated point spread functions to simulate a focused cone of light. The preoperative point spread function of FIG. 34A is from a patient with presbyopia. The patient received a multi-focal ablation, and the post operative volumetric point spread function of FIG. 34B shows an improved depth of focus, extending the patient's reading range to almost two diopters. A comparison of the preoperative and postoperative volumetric point spread functions for the patient is shown, from another view, in FIG. 34C.

Snellen reading charts evolved from the pre-operative and post-operative point spread functions of the presbyopic treatment study patient are shown in FIGS. 35A and 35C, respectively. FIG. 35B illustrates a detailed section of the pre-treatment Snellen chart evolved from the point spread function, while FIG. 35D shows a similar detailed view for the post-treatment Snellen chart. These Snellen charts are all for far viewing distances.

The benefit of the presbyopia treatment is more clearly seen in the reading distance (at two diopters) Snellen charts (FIGS. 35E and 35F) as compared to the post-treatment Snellen charts (FIGS. 35G and 35H). The post-presbyopia treatment Snellen chart shows significant improvement in near visual perception, and indicates a much improved reading-distance visual acuity provided by the presbyopia treatment. The reading distance Snellen charts are calculated using the +2.0 D point spread function indicated in the front of the illustration shown in FIGS. 34A and 34B, while the distance Snellen charts are calculated using the 0.0 D point spread function shown in the middle of the volumetric point spread function illustrations.

Figures 10, 36:
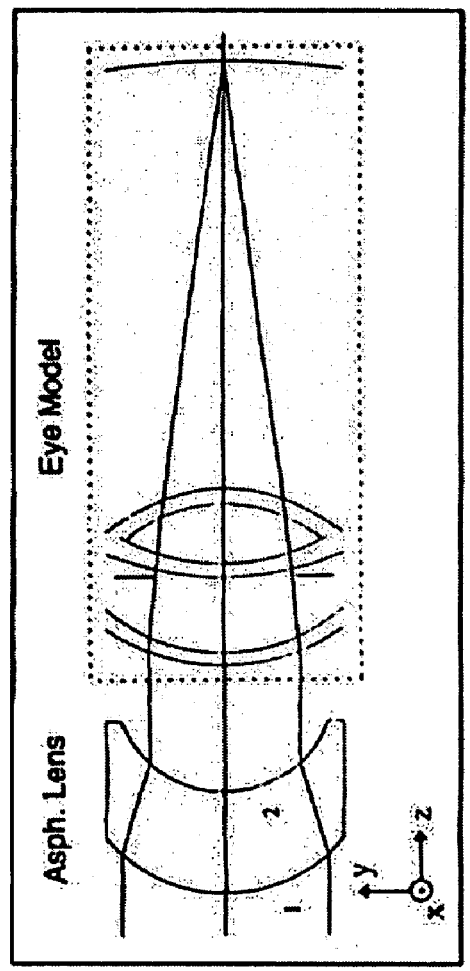
FIG. 36 illustrates a schematic diagram of an eye model used for calculations described herein, along with associated lens parameters.

Referring now to FIG. 36, a schematic diagram of an eye model with an aspheric correcting lens for on-axis retinal imaging is shown, as may be used for some of the calculations described herein. The table of FIG. 36 shows associated correcting lens parameters for on-axis correction.

Referring now to FIGS. 37A, 37B, and 37C, a comparison of these illustrations and their associated Strehl ratios provides an indication on how meaningful that parameter is. In FIG. 37B, a diffraction limited point spread function is shown. FIG. 37A shows a patient point spread function using white light. The white light Strehl ratio is 0.56. The point spread function of FIG. 37C is shown for 550 nm light, giving a traditional 550 nm Strehl ratio of 0.21.

Figure 38:
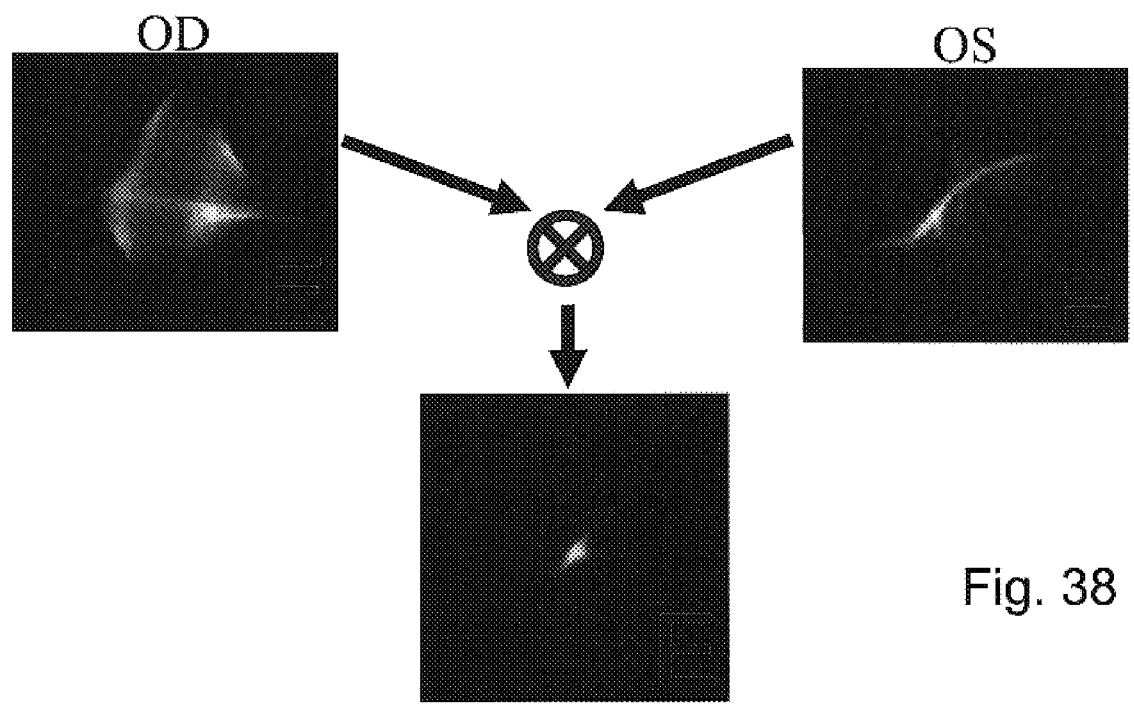
FIG. 38 illustrates the effects of binocular image processing.

As can be understood with reference to FIG. 38, still further elements or effects of vision may be incorporated into the perceived point spread function model. For example, a right point spread function OD and a left point spread function OS are both viewed by a patient using right and left eyes, and the two images are processed using binocular image processing to generate a combined point spread function.

Figure 39B:
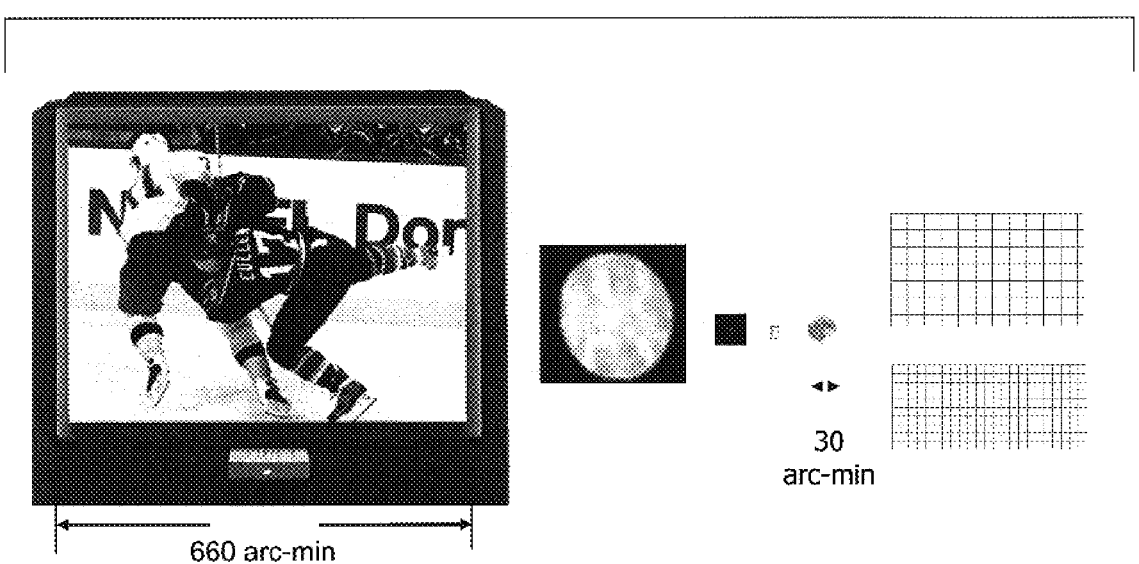

Referring now to FIGS. 39A and 39B, there can be scale issues when reviewing point spread functions. For example, in FIG. 39B, watching television may involve a scale of about 660 arc-min, optionally making use of a 27 inch screen at eight feet, or a 54 inch screen at 16 feet. Associated point spread functions during such television viewing may or may not have a significant impact on visual perception. Viewing of the moon may also be impacted by differing point spread functions. A fine scale as illustrated on the right side of FIG. 39B may also have an impact. Referring now to FIG. 40, point spread function zoom may be illustrated.

Figure 41:
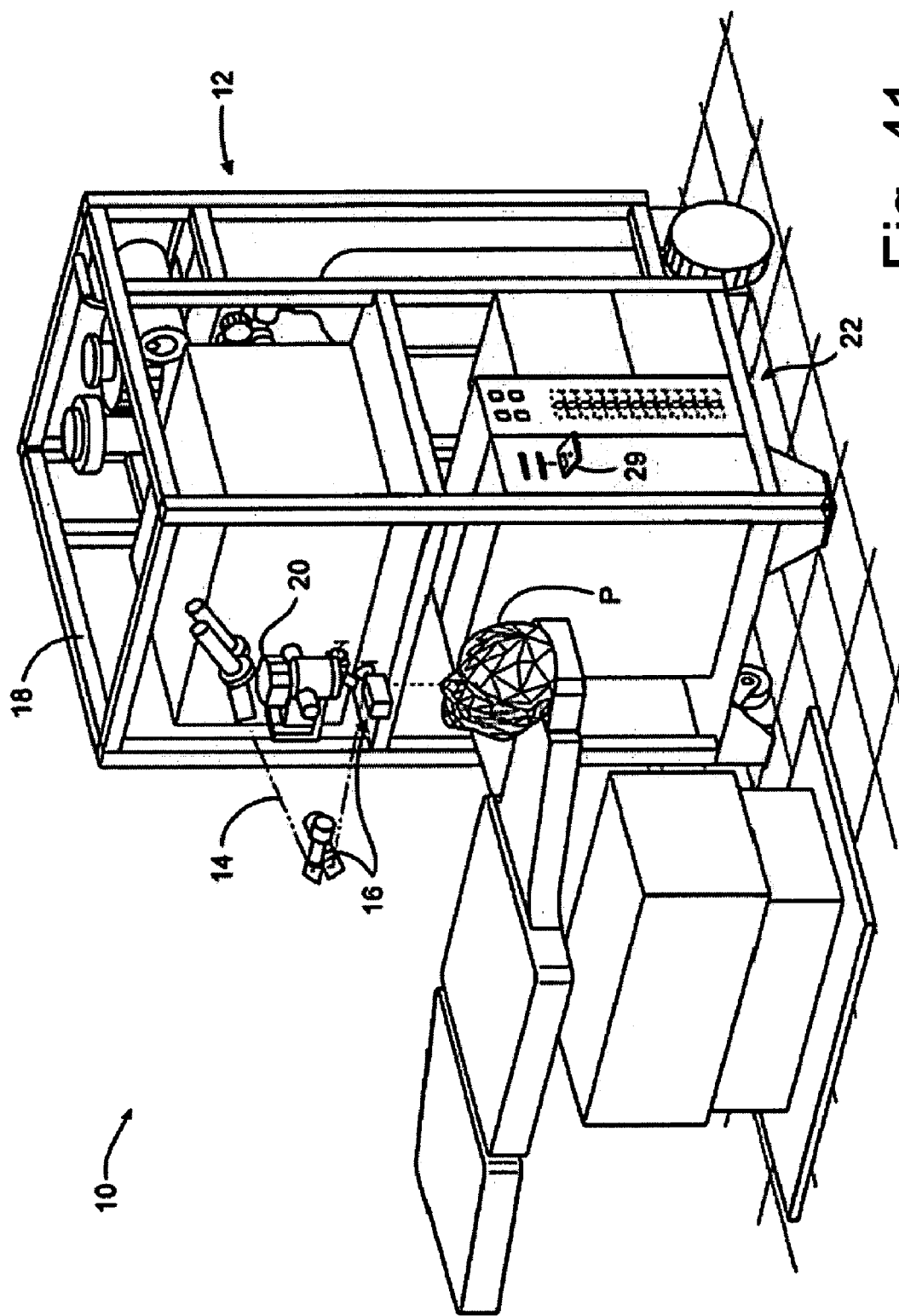
FIG. 41 illustrates a laser ablation system according to an embodiment of the invention.

Referring now to FIG. 41, a laser eye surgery system 10 includes a laser 12 that produces a laser beam 14. Laser 12 is optically coupled to laser delivery optics 16, which directs laser beam 14 to an eye of patient P. A delivery optics support structure (not shown here for clarity) extends from a frame 18 supporting laser 12. A microscope 20 is mounted on the delivery optics support structure, the microscope often being used to image a cornea of the eye.

Laser 12 generally comprises an Excimer laser, ideally comprising an argon-fluorine laser producing pulses of laser light having a wavelength of approximately 193 nm. Laser 12 will preferably be designed to provide a feedback stabilized fluence at the patient's eye, delivered via laser delivery optics 16. The present invention may also be useful with alternative sources of ultraviolet or infrared radiation, particularly those adapted to controllably ablate or otherwise reshape the corneal tissue without causing significant damage to adjacent and/or underlying tissues of the eye. In alternate embodiments, the laser beam source employs a solid state laser source having a wavelength between 193 and 215 nm as described in U.S. Pat. Nos. 5,520,679 and 5,144,630 to Lin, and 5,742,626 to Mead, the full disclosures of which are incorporated herein by reference. In another embodiment, the laser source is an infrared laser as described in U.S. Pat. Nos. 5,782,822 and 6,090,102 to Telfair, the full disclosures of which are incorporated herein by reference. Hence, although an excimer laser is the illustrative source of an ablating beam, other lasers may be used in the present invention.

Laser 12 and laser delivery optics 16 will generally direct laser beam 14 to the eye of patient P under the direction of a computer system 22. Computer system 22 will often selectively adjust laser beam 14 to expose portions of the cornea to the pulses of laser energy so as to effect a predetermined sculpting of the cornea and alter the refractive characteristics of the eye. In many embodiments, both laser 12 and the laser delivery optical system 16 will be under control of computer system 22 to effect the desired laser sculpting process, with the computer system effecting (and optionally modifying) the pattern of laser pulses. The pattern of pulses may be summarized in machine readable data of tangible media 29 in the form of a treatment table, and the treatment table may be adjusted according to feedback input into computer system 22 from an automated image analysis system (or manually input into the processor by a system operator) in response to real-time feedback data provided from an ablation monitoring system feedback system. The laser treatment system 10, and computer system 22 may continue and/or terminate a sculpting treatment in response to the feedback, and may optionally also modify the planned sculpting based at least in part on the feedback.

Additional components and subsystems may be included with laser system 10, as should be understood by those of skill in the art. For example, spatial and/or temporal integrators may be included to control the distribution of energy within the laser beam, as described in U.S. Pat. No. 5,646,791, the full disclosure of which is incorporated herein by reference. Ablation effluent evacuators/filters, aspirators, and other ancillary components of the laser surgery system are known in the art. Further details of suitable systems for performing a laser ablation procedure can be found in the patent literature. Suitable systems also include commercially available refractive laser systems such as those manufactured and/or sold by Alcon, Bausch & Lomb, Nidek, WaveLight, LaserSight, Schwind, Zeiss Meditec, and the like.

Figure 42:
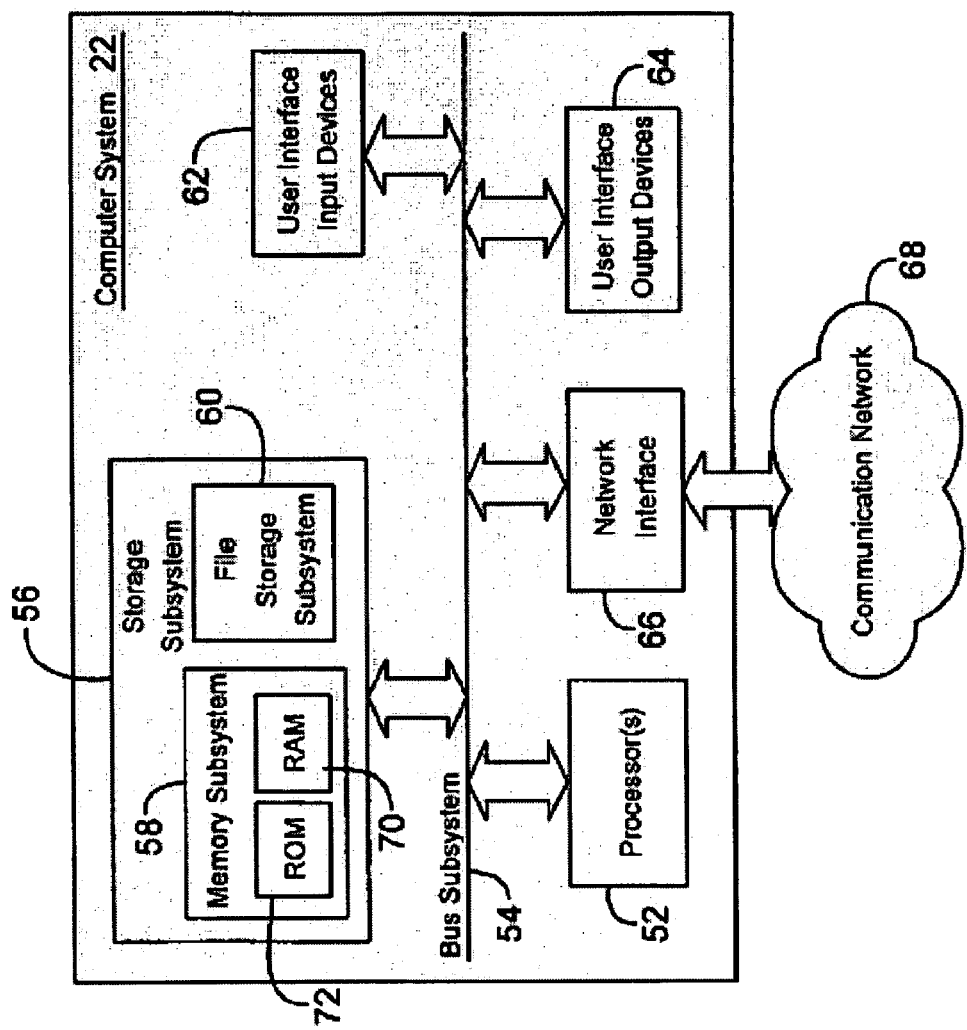
FIG. 42 schematically illustrates a computer of the ablation system of FIG. 41.

FIG. 42 is a simplified block diagram of an exemplary computer system 22 that may be used by the laser surgical system 10 of the present invention. Computer system 22 typically includes at least one processor 52 which may communicate with a number of peripheral devices via a bus subsystem 54. These peripheral devices may include a storage subsystem 56, comprising a memory subsystem 58 and a file storage subsystem 60, user interface input devices 62, user interface output devices 64, and a network interface subsystem 66. Network interface subsystem 66 provides an interface to outside networks 68 and/or other devices, such as the wavefront measurement system 30.

User interface input devices 62 may include a keyboard, pointing devices such as a mouse, trackball, touch pad, or graphics tablet, a scanner, foot pedals, a joystick, a touchscreen incorporated into the display, audio input devices such as voice recognition systems, microphones, and other types of input devices. User input devices 62 will often be used to download a computer executable code from a tangible storage media 29 embodying any of the methods of the present invention. In general, use of the term "input device" is intended to include a variety of conventional and proprietary devices and ways to input information into computer system 22.

User interface output devices 64 may include a display subsystem, a printer, a fax machine, or non-visual displays such as audio output devices. The display subsystem may be a cathode ray tube (CRT), a flat-panel device such as a liquid crystal display (LCD), a projection device, or the like. The display subsystem may also provide a non-visual display such as via audio output devices. In general, use of the term "output device" is intended to include a variety of conventional and proprietary devices and ways to output information from computer system 22 to a user, while a graphical display encompasses such devices as monitors, printers, LCD screens, and the like which are suitable for displaying graphs, images and other graphical information.

Storage subsystem 56 stores the basic programming and data constructs that provide the functionality of the various embodiments of the present invention. For example, a database and modules implementing the functionality of the methods of the present invention, as described herein, may be stored in storage subsystem 56. These software modules are generally executed by processor 52. In a distributed environment, the software modules may be stored on a plurality of computer systems and executed by processors of the plurality of computer systems. Storage subsystem 56 typically comprises memory subsystem 58 and file storage subsystem 60.

Memory subsystem 58 typically includes a number of memories including a main random access memory (RAM) 70 for storage of instructions and data during program execution and a read only memory (ROM) 72 in which fixed instructions are stored. File storage subsystem 60 provides persistent (non-volatile) storage for program and data files, and may include tangible storage media 29 (FIG. 41) which may optionally embody wavefront sensor data, wavefront gradients, a wavefront elevation map, a treatment map, and/or an ablation table. File storage subsystem 60 may include a hard disk drive, a floppy disk drive along with associated removable media, a Compact Digital Read Only Memory (CD-ROM) drive, an optical drive, DVD, CD-R, CD-RW, solid-state removable memory, and/or other removable media cartridges or disks. One or more of the drives may be located at remote locations on other connected computers at other sites coupled to computer system 22. The modules implementing the functionality of the present invention may be stored by file storage subsystem 60.

Bus subsystem 54 provides a mechanism for letting the various components and subsystems of computer system 22 communicate with each other as intended. The various subsystems and components of computer system 22 need not be at the same physical location but may be distributed at various locations within a distributed network. Although bus subsystem 54 is shown schematically as a single bus, alternate embodiments of the bus subsystem may utilize multiple busses.

Computer system 22 itself can be of varying types including a personal computer, a portable computer, a workstation, a computer terminal, a network computer, a control system in a wavefront measurement system or laser surgical system, a mainframe, or any other data processing system. Due to the ever-changing nature of computers and networks, the description of computer system 22 depicted in FIG. 42 is intended only as a specific example for purposes of illustrating one embodiment of the present invention. Many other configurations of computer system 22 are possible having more or less components than the computer system depicted in FIG. 2, and the processor of system 10 may at least in part be integrated into the processor of FIG. 43.

Referring now to FIG. 3, one embodiment of a wavefront measurement system 30 is schematically illustrated in simplified form. In very general terms, wavefront measurement system 30 is configured to sense local slopes of a gradient map exiting the patient's eye. Devices based on the Hartmann-Shack principle generally include a lenslet array to sample the gradient map uniformly over an aperture, which is typically the exit pupil of the eye. Thereafter, the local slopes of the gradient map are analyzed so as to reconstruct the wavefront surface or map.

More specifically, one wavefront measurement system 30 includes an image source 32, such as a laser, which projects a source image through optical tissues 34 of eye E so as to form an image 44 upon a surface of retina R. The image from retina R is transmitted by the optical system of the eye (e.g., optical tissues 34) and imaged onto a wavefront sensor 36 by system optics 37. The wavefront sensor 36 communicates signals to a computer system 22' for measurement of the optical errors in the optical tissues 34 and/or determination of an optical tissue ablation treatment program. Computer 22' may include the same or similar hardware as the computer system 22 illustrated in FIGS. 1 and 2. Computer system 22' may be in communication with computer system 22 that directs the laser surgery system 10, or some or all of the components of computer system 22, 22' of the wavefront measurement system 30 and laser surgery system 10 may be combined or separate. If desired, data from wavefront sensor 36 may be transmitted to a laser computer system 22 via tangible media 29, via an I/O port, via an networking connection 66 such as an intranet or the Internet, or the like.

Wavefront sensor 36 generally comprises a lenslet array 38 and an image sensor 40. As the image from retina R is transmitted through optical tissues 34 and imaged onto a surface of image sensor 40 and an image of the eye pupil P is similarly imaged onto a surface of lenslet array 38, the lenslet array separates the transmitted image into an array of beamlets 42, and (in combination with other optical components of the system) images the separated beamlets on the surface of sensor 40. Sensor 40 typically comprises a charged couple device or "CCD," and senses the characteristics of these individual beamlets, which can be used to determine the characteristics of an associated region of optical tissues 34. In particular, where image 44 comprises a point or small spot of light, a location of the transmitted spot as imaged by a beamlet can directly indicate a local gradient of the associated region of optical tissue.

Eye E generally defines an anterior orientation ANT and a posterior orientation POS. Image source 32 generally projects an image in a posterior orientation through optical tissues 34 onto retina R as indicated in FIG. 3. Optical tissues 34 again transmit image 44 from the retina anteriorly toward wavefront sensor 36. Image 44 actually formed on retina R may be distorted by any imperfections in the eye's optical system when the image source is originally transmitted by optical tissues 34. Optionally, image source projection optics 46 may be configured or adapted to decrease any distortion of image 44.

In some embodiments, image source optics 46 may decrease lower order optical errors by compensating for spherical and/or cylindrical errors of optical tissues 34. Higher order optical errors of the optical tissues may also be compensated through the use of an adaptive optics system, such as a deformable mirror (described below). Use of an image source 32 selected to define a point or small spot at image 44 upon retina R may facilitate the analysis of the data provided by wavefront sensor 36. Distortion of image 44 may be limited by transmitting a source image through a central region 48 of optical tissues 34 which is smaller than a pupil 50, as the central portion of the pupil may be less prone to optical errors than the peripheral portion. Regardless of the particular image source structure, it will be generally be beneficial to have a well-defined and accurately formed image 44 on retina R.

The wavefront data may be stored in a computer readable medium 29 or a memory of the wavefront sensor system 30 in two separate arrays containing the x and y wavefront gradient values obtained from image spot analysis of the Hartmann-Shack sensor images, plus the x and y pupil center offsets from the nominal center of the Hartmann-Shack lenslet array, as measured by the pupil camera 51 (FIG. 43) image. Such information contains all the available information on the wavefront error of the eye and is sufficient to reconstruct the wavefront or any portion of it. In such embodiments, there is no need to reprocess the Hartmann-Shack image more than once, and the data space required to store the gradient array is not large. For example, to accommodate an image of a pupil with an 8 mm diameter, an array of a 20×20 size (i.e., 400 elements) is often sufficient. As can be appreciated, in other embodiments, the wavefront data may be stored in a memory of the wavefront sensor system in a single array or multiple arrays.

While the methods of the present invention will generally be described with reference to sensing of an image 44, it should be understood that a series of wavefront sensor data readings may be taken. For example, a time series of wavefront data readings may help to provide a more accurate overall determination of the ocular tissue aberrations. As the ocular tissues can vary in shape over a brief period of time, a plurality of temporally separated wavefront sensor measurements can avoid relying on a single snapshot of the optical characteristics as the basis for a refractive correcting procedure. Still further alternatives are also available, including taking wavefront sensor data of the eye with the eye in differing configurations, positions, and/or orientations. For example, a patient will often help maintain alignment of the eye with wavefront measurement system 30 by focusing on a fixation target, as described in U.S. Pat. No. 6,004,313, the full disclosure of which is incorporated herein by reference. By varying a position of the fixation target as described in that reference, optical characteristics of the eye may be determined while the eye accommodates or adapts to image a field of view at a varying distance and/or angles.

Figure 43A:
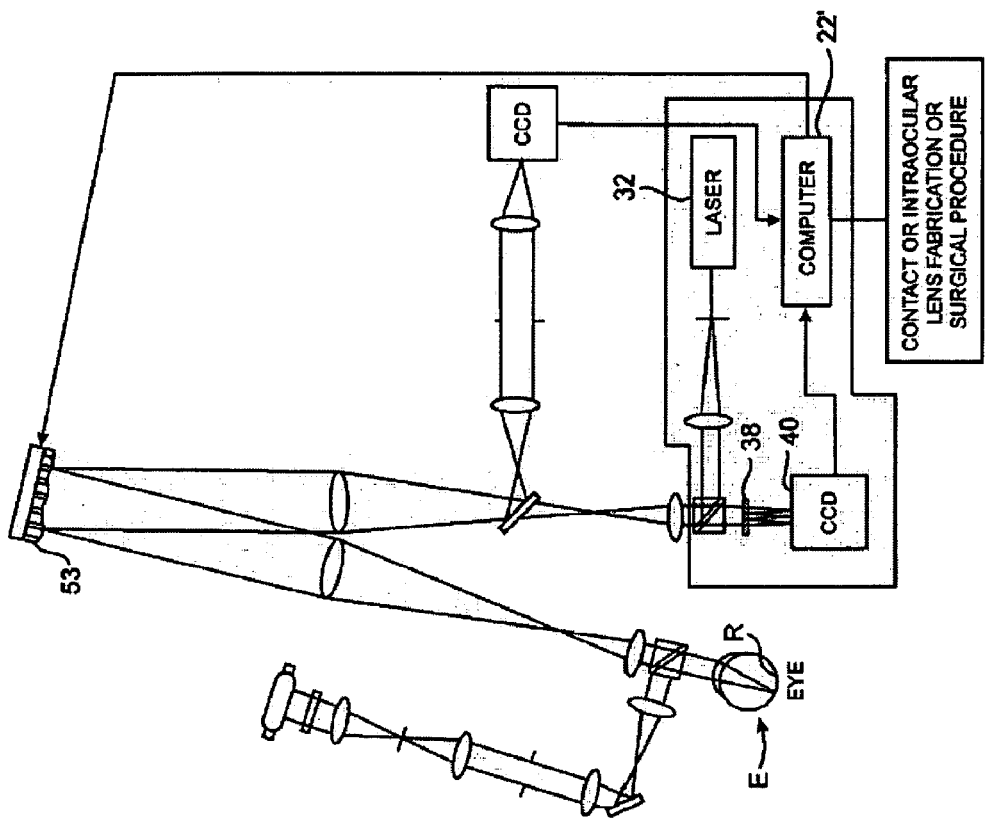
FIG. 43A illustrates an alternative wavefront measurement system according to an embodiment of the present invention.

An alternative embodiment of a wavefront measurement system is illustrated in FIG. 43A. The major components of the system of FIG. 43A are similar to those of FIG. 3. Additionally, FIG. 43A includes an adaptive optics system 53 in the form of a deformable mirror. The source image is reflected from deformable mirror 98 during transmission to retina R, and the deformable mirror is also along the optical path used to form the transmitted image between retina R and imaging sensor 40. Deformable mirror 98 can be controllably deformed by computer system 22 to limit distortion of the image formed on the retina or of subsequent images formed of the images formed on the retina, and may enhance the accuracy of the resultant wavefront data. The structure and use of the system of FIG. 43A are more fully described in U.S. Pat. No. 6,095,651, the full disclosure of which is incorporated herein by reference.

The components of an embodiment of a wavefront measurement system for measuring the eye and ablations comprise elements of a VISX WaveScan® system, available from VISX, Incorporated of Santa Clara, Calif. One embodiment includes a WaveScan® system with a deformable mirror as described above. An alternate embodiment of a wavefront measuring system is described in U.S. Pat. No. 6,271,915, the full disclosure of which is incorporated herein by reference.

Figure 43:
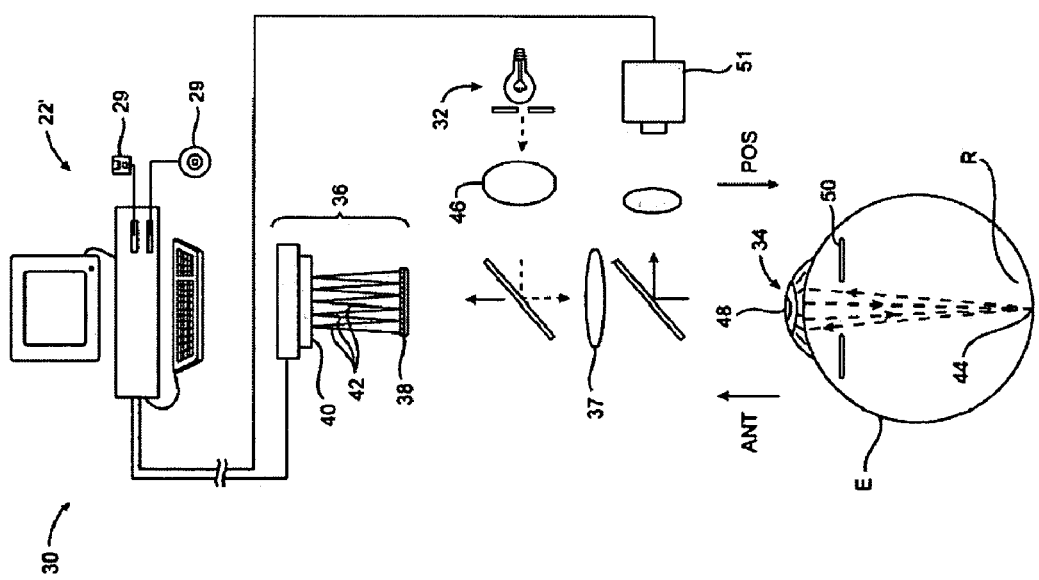
FIG. 43 schematically illustrates a wavefront measurement system according to an embodiment of the present invention, as may be used to measure wavefronts and generate wavefront signals for determining point spread functions of a patient's eye.

Each of the point spread function calculations and modifications described above may be performed using computer system 22 of FIGS. 41 and 42, processor 30 of FIG. 43 computer 22' of FIG. 43, and/or some other computer or other processor having appropriate hardware, software, and/or firmware. The various calculations and method steps described herein may be performed by modules, and the modules may comprise any of a wide variety of digital and/or analog data processing hardware and/or software arranged to perform the method steps described herein. The modules optionally comprising data processing hardware adapted to perform one or more of these steps by having appropriate machine programming code associated therewith, the modules for two or more steps (or portions of two or more steps) being integrated into a single processor board or separated into different processor boards in any of a wide variety of integrated and/or distributed processing architectures. These methods and systems will often employ a tangible media embodying machine-readable code with instructions for performing the method steps described above. Suitable tangible media may comprise a memory (including a volatile memory and/or a non-volatile memory), a storage media (such as a magnetic recording on a floppy disk, a hard disk, a tape, or the like; on an optical memory such as a CD, a CD-R/W, a CD-ROM, a DVD, or the like; or any other digital or analog storage media), or the like.

For the analytical solutions described herein, some or all of the method steps may be performed with computer processors of modest capability, i.e., a 386 processor from Intel™ may be enough to calculate the Zernike coefficients, and even 286 processor may be fine. Scaling of Zernike coefficients was described by Jim Schweigerling, in a publication entitled "Scaling Zernike Expansion Coefficients to Different Pupil Sizes," *J. Opt. Soc. Am. A*, 19 (10), pp 1937-1945 (10/2002). No special memory is needed (i.e., no buffers, all can be done as regular variables or using registers). Also, suitable code can be written in any of a wide variety of computer languages, with the exemplary embodiment employing C++. This exemplary embodiment may comprise, for example, code which performs the Zernike coefficient calculations and/or Fourier reconstructions, visual effect modeling, and provides graphical output, and the like.

Summarizing some of the above, to generate a realistic point spread function, the following effects were added to a point spread function model and described above: polychromatic light sources; chromatic aberration of the eye; wavelength-dependent visual response (to photopic and scotopic conditions); adjustable pupil sizes; Stiles-Crawford effect; and non-linear retinal responses; among others. Each effect was tested independently and in combination with other effects. All effects caused significant changes in the appearance of the point spread function, with the most significant change being caused by a combination of a polychromatic light source, the chromatic aberration, and wavelength-dependent visual response. By combining these effects with human color sensitivity (mapping wavelengths to red, green, and blue intensities) a color point spread function can be generated.

The retina demonstrates a logarithmic sensitivity to light that has usually not been included when generating point spread functions. It was found that this effect significantly changed the appearance of the point spread function and therefore that it should be modeled when practical. The theoretical pupil size was varied, causing both the size and shape of the point spread function to change significantly. This indicates that when analyzing or viewing a point spread function the pupil size should be included in the model.

The Stiles-Crawford effect was found to have the least impact of the effects listed above. The effect was largest for patients with large pupils, but even in those cases, did not fundamentally alter the point spread function image.

The results of the wavefront accuracy comparisons indicate that sixth order Zernike reconstruction is not sufficient to generate a fully accurate point spread function. The general sizes and shapes were similar, but the Fourier-based images showed many features that were not physical in the Zernike-based images.

The retinal wavelength response function shifts from photopic conditions (having a peak sensitivity at 550 mn) to scotopic conditions (with a peak sensitivity of 507 mn). A daytime and nighttime point spread function can thus be calculated from the same wavelength by allowing the model to shift from one function (optionally modeling wavelength response at photopic conditions) to another (modeling response at scotopic conditions). Analysis shows that most patients experience a shift towards myopia under nighttime conditions. This myopic shift may be explained by the scotopic eye's preference for blue light, which has a greater chromatic shift. This analysis may be useful for patients complaining of night myopia.

While the exemplary embodiments have been described in some detail, by way of example and for clarity of understanding, those of skill in the art will recognize that a variety of modification, adaptations, and changes may be employed. Hence, the scope of the present invention should be limited solely by the appended claims.

What is claimed is:

1. A system for evaluating or treating an eye, the system comprising:
   an input for receiving an optical aberration signal;
   a processor coupled to the input, the processor comprising a module with storage media embodying processor executable software for determining a volumetric point spread function from the aberration signal, the volumetric point spread function comprising a point spread function at a plurality of locations spread throughout a distance range from a cornea of the eye, the retina being disposed in the distance range; and
   an output coupled to the module, the output transmitting signals in response to the volumetric point spread function.

2. The system of claim 1, wherein the input is coupled to a wavefront sensor.

3. The system of claim 2, wherein the output signals indicate an optical performance of the eye.

4. The system of claim 1, wherein the output is coupled to a refractive laser system.

5. The system of claim 4, wherein the processor derives a pattern of laser energy to improve refractive performance of the eye in response to the output signal from the module.

6. The system of claim 1, wherein the module determines the volumetric point spread function at a plurality of different pupil sizes.

7. The system of claim 1, wherein the module determines the volumetric point spread function at photopic conditions.

8. The system of claim 1, wherein the module determines the volumetric point spread function at scotopic conditions.

9. The system of claim 1, wherein the output signals correspond to a graphical representation of the volumetric point spread function.

10. The system of claim 9, wherein the graphical representation of the volumetric point spread function corresponds to perceived vision of a patient, the module configured to generate the volumetric point spread function by modeling one or more visual effects selected from:
    polychromatic source light;
    chromatic aberration of the eye;
    wavelength-dependent visual response to photopic and scotopic conditions;
    adjustable pupil size;
    Stiles-Crawford effect; and
    non-linear retinal response.

11. The system of claim 9, wherein the module is configured to generate a post-treatment volumetric point spread function, the graphical representation allowing a comparison of the volumetric point spread function with the post-treatment volumetric point spread function.

12. The system of claim 11, wherein the post-treatment volumetric point spread function indicates an extension of a reading range by at least about 2 diopters.

13. A system for evaluating or treating an eye of a particular patient, the eye having optical aberration, the system comprising:
    an input for receiving an optical aberration signal corresponding to the aberration of the eye;
    a processor coupled to the input, the processor comprising a module with storage media embodying processor executable software configured to determine a perceived point spread function, the perceived point spread function further comprising a volumetric point spread function, the volumetric point spread function comprising a point spread function at a plurality of locations spread throughout a distance range from a cornea of the eye, the retina being disposed in the distance range, the perceived point spread function determined from the aberration signal by modeling of:
    a) chromatic aberration of the eye; and
    b) adjustable pupil size of the eye; and
    an output coupled to the module, the output transmitting signals in response to the perceived point spread function.

14. The system of claim 13, wherein the module is further configured to model one or more visual effects selected from:
    c) polychromatic source light;
    d) wavelength-dependent visual response to photopic and scotopic conditions; and
    e) non-linear retinal response.

15. The system of claim 14, wherein the module is further configured to model each of c)-e).

16. The system of claim 15, wherein the module is further configured to model Stiles-Crawford effect.

17. The system of claim 15, wherein the system does not model Stiles-Crawford effect.

18. The system of claim 15, further comprising a graphical display coupled to the output, the graphical display illustrating the perceived point spread function so as to model visual perception of the patient in response to an image.

19. The system of claim 16, further comprising a graphical display coupled to the output, the graphical display illustrating the perceived point spread function at the plurality of locations.

20. A method for evaluating or treating an eye of a particular patient, the eye having optical aberration, the method comprising:
    identifying the optical aberration of the eye;
    determining a volumetric point spread function from the aberration; and
    graphically displaying the determined point spread function, the graphical display of the volumetric point spread function including point spread functions displayed at a plurality of locations spread throughout a distance range from a cornea of the eye, the retina being disposed within the distance range.

21. The method of claim 20, wherein the determined point spread function comprises a perceived point spread function, the graphical display of the point spread function corresponding to perceived vision of a patient, the module configured to generate the volumetric point spread function by modeling one or more visual effects selected from:
    polychromatic source light;
    chromatic aberration of the eye;
    wavelength-dependent visual response to photopic and scotopic conditions;
    adjustable pupil size;
    Stiles-Crawford effect; and
    non-linear retinal response.

22. The method of claim 20, further comprising showing the graphical display to the patient to objectively validate the patient's perception or the determined point spread function.

23. The method of claim 20, further comprising developing a refractive treatment prescription using the graphical display.

* * * * *

UNITED STATES PATENT AND TRADEMARK OFFICE
CERTIFICATE OF CORRECTION

| | |
|---|---|
| PATENT NO. | : 7,377,648 B2 |
| APPLICATION NO. | : 11/064876 |
| DATED | : May 27, 2008 |
| INVENTOR(S) | : Erik Gross et al. |

Page 1 of 1

It is certified that error appears in the above-identified patent and that said Letters Patent is hereby corrected as shown below:

Column 22, Claim 19: "claim 16" should be deleted and replaced by --claim 15--

Signed and Sealed this

Twenty-sixth Day of August, 2008

JON W. DUDAS
*Director of the United States Patent and Trademark Office*

UNITED STATES PATENT AND TRADEMARK OFFICE
CERTIFICATE OF CORRECTION

PATENT NO. : 7,377,648 B2  Page 1 of 1
APPLICATION NO. : 11/064876
DATED : May 27, 2008
INVENTOR(S) : Erik Gross et al.

It is certified that error appears in the above-identified patent and that said Letters Patent is hereby corrected as shown below:

Column 22, Claim 19, line 30: "claim 16" should be deleted and replaced by --claim 15--

This certificate supersedes the Certificate of Correction issued August 26, 2008.

Signed and Sealed this

Twenty-third Day of September, 2008

JON W. DUDAS
*Director of the United States Patent and Trademark Office*